(12) United States Patent
Tsipouras et al.

(10) Patent No.: US 7,522,757 B2
(45) Date of Patent: Apr. 21, 2009

(54) METHOD AND APPARATUS FOR COMPUTER CONTROLLED CELL BASED DIAGNOSIS

(75) Inventors: Petros Tsipouras, Madison, CT (US); Triantafyllos Tafas, Rocky Hill, CT (US)

(73) Assignee: Ikonisys, Inc., New Haven, CT (US)

( * ) Notice: Subject to any disclaimer, the term of this patent is extended or adjusted under 35 U.S.C. 154(b) by 0 days.

(21) Appl. No.: 11/264,273

(22) Filed: Nov. 1, 2005

(65) Prior Publication Data

US 2006/0072805 A1 Apr. 6, 2006

Related U.S. Application Data

(63) Continuation of application No. 10/130,559, filed as application No. PCT/US99/27608 on Nov. 18, 1999.

(51) Int. Cl.
*G06K 9/00* (2006.01)

(52) U.S. Cl. .................. 382/133; 382/134; 382/128

(58) Field of Classification Search .......... 382/128–134
See application file for complete search history.

(56) References Cited

U.S. PATENT DOCUMENTS

| | | | |
|---|---|---|---|
| 4,513,438 A | 4/1985 | Graham et al. |
| 4,983,044 A | 1/1991 | Schweber |
| 5,352,613 A | 10/1994 | Tafas et al. |
| 5,740,269 A | 4/1998 | Oh et al. |
| 5,764,792 A | 6/1998 | Kennealy |
| 5,889,881 A | 3/1999 | MacAulay et al. |
| 6,136,540 A | 10/2000 | Tsipouras et al. |
| 6,221,596 B1 | 4/2001 | Yemini et al. |

FOREIGN PATENT DOCUMENTS

EP 0 595 506 5/1994

(Continued)

OTHER PUBLICATIONS

Baxes, 1994, "Digital Image Processing, Passage," U.S., New York, Wiley, pp. 127-137.

(Continued)

*Primary Examiner*—Wesley Tucker
(74) *Attorney, Agent, or Firm*—Kelley Drye & Warren LLP

(57) ABSTRACT

A computer controlled method for detecting and diagnosing a rare cell type in a tissue sample is provided, said method comprising treating the tissue sample such that it generates a first signal indicative of the presence at a location of a rare cell, detecting the first signal, treating the location at which the first signal is detected to generate a second signal indicative of a diagnostically useful cellular characteristic and detecting the second signal. The first signal can be morphological or a color present in a sought cell either before or after staining. The second signal can be generated by in situ PCR or PCR in situ hybridization. In one preferred embodiment, the rare cell type is a fetal cell in a maternal blood tissue sample, said sample consisting of a smear of unenriched maternal blood. In another embodiment, the method is used to diagnose or genotype cancer cells in a blood or tissue biopsy sample.

16 Claims, 13 Drawing Sheets

FOREIGN PATENT DOCUMENTS

| | | |
|---|---|---|
| EP | 0 713 086 B1 | 4/1999 |
| WO | WO 93/18186 | 9/1993 |
| WO | WO 94/02646 | 2/1994 |
| WO | WO 97/20198 | 6/1997 |
| WO | WO 97/43732 | 11/1997 |
| WO | WO 99/02960 | 1/1999 |
| WO | WO 99 08091 | 2/1999 |
| WO | WO 01/37192 A1 | 11/1999 |
| WO | WO 99/58972 | 11/1999 |

OTHER PUBLICATIONS

Lizardi, et al., 1998, "Mutation Detection and Single-Molecule Counting Using Isothermal Rooling-Circle Amplification," Nature Genetics, 19(3):225-232.

Mesker, et al., 1994, "Detection of Immunocytochemically Stained Rare Events Using Image Analysis," Ctyochemistry 17:209-215.

Oosterwijk, et al., 1998, "Strategies for Rare-Event Detection: An Approach for Automated Fetal Cell Detection in Maternal Blood," Am. J. Hum. Genet. 63:1783-1792.

Oosterwijk, et al., 1998, "Development of a Preparation and Staining Method for Fetal Erythroblasts in Maternal Blood: Simultaneous Immunocytochemical Staining and FISH Analysis," Cytometry 32:170-177.

Oosterwijk, et al., 1998, "Fetal Cell Detection in Maternal Blood: A Study in 236 Samples Using Erythroblast Morphology, DAB and HbF Staining, and FISH Analysis," Cytometry 32:178-185.

Tanke, et al., 1996, "Detection of "Rare Event" Fetal Erythroblasts in Maternal Blood Using Automated Microscopy," Early Hum. Devel. 47 Suppl.:S89-S93.

Verwoerd, et al., 1987, "Somatic Cell Mutations in Humans Detected by Image Analysis of Immunofluorescently Stained Erythrocytes," in: Clinical Cytometry and Histometry, Burger et al., eds., Academic Press, pp. 465-469.

"XL Vision Announces Advanced Imaging Technology For Early Detection of Metastatic Cancer," Press Release dated Dec. 18, 1995, XL Vision, Sebastian, FL, pp. 7-11.

METHOD AND APPARATUS FOR COMPUTER CONTROLLED CELL BASED DIAGNOSIS

This application is a continuation of U.S. application Ser. No. 10/130,559, filed on May 17, 2002, which is a national phase application of PCT/US99/27608 (WO 01/37192), filed on Nov. 18, 1999, which disclosures are herein incorporated by reference in their entirety.

1. FIELD OF THE INVENTION

The present invention relates to computer controlled methods and apparatus for obtaining and preparing cell samples and for identifying a rare cell of interest from a field of cells and making a diagnosis based on a characteristic of a rare cell selected in the field. In one important embodiment, the invention relates to obtaining and preparing a maternal blood sample for fetal cell based prenatal diagnosis. Diagnosis performed by embodiments of the invention includes employing a computer to identify, characterize, and count objects in the optical field which are tagged using fluorescence in situ hybridization to visualize selected objects in the optical field.

2. BACKGROUND OF THE INVENTION

The advent of DNA based prenatal diagnosis for human genetic disorders has led to the development of a number of new diagnostic methods. These diagnostic methods permit early detection and consequently informed decisions and intervention with respect to fetus having a genetic disorder. These methods, however, have a number of disadvantages. Each of the new diagnostic methods with which this discussion is concerned requires that a sample of isolated fetal cells be obtained, so that the DNA of the fetus may be examined or tested for signs of specific genetic disorders.

The disadvantages of these modern methods are at least two-fold. First, there is a need to obtain a sample of fetal cells. Currently, fetal cells are obtained by invasive procedures requiring obstetric intervention by amniocentesis or by chorionic villus sampling. These highly specialized procedures carry a small, but significant, risk to the fetus. Early in pregnancy, the level of risk to the fetus is high and the number of cells obtained is low. Therefore, results of these procedures often are not obtained until 18-20 weeks of pregnancy. Second, accurately assessing, quantifying, and assigning a significance to images of cells is difficult, time-consuming and unacceptably subjective.

One modem procedure for obtaining fetal cells relies on leakage of fetal cells into the maternal circulation. By simply drawing a sample of maternal blood, it is theoretically possible to obtain fetal cell material in a sufficient quantity for prenatal diagnosis by DNA based methods. Obtaining fetal cells from the maternal blood circulation avoids any risk to the fetus and can be undertaken as early as 10-12 weeks of pregnancy.

Fetal cells which have been detected in the maternal blood circulation include trophoblasts, lymphocytes and nucleated erythrocytes. Trophoblasts were the first fetal cells to be identified in the maternal blood circulation, due to their large size. However, nucleated erythrocytes have generated the greatest degree of interest as sources of genetic material for prenatal diagnosis due to their rarity in the adult blood circulation, their abundance in fetal blood and their limited life span. These factors combine to reduce errors in distinguishing fetal cell material from maternal cell material. Fetal cells circulating in the maternal blood have a life span ranging from a few weeks (for the nucleated erythrocytes) to a few years (for the lymphocytes).

Although they are consistently present in the maternal blood circulation, fetal cells are very rare, severely limiting their diagnostic utility. Estimates of the concentration of fetal cells within the maternal blood circulation vary widely, from a high level of 1 fetal cell in $10^5$ maternal cells, to a low level of one fetal cell in $10^9$ maternal cells. Thus, a 10 ml sample of maternal blood will ordinarily contain between about 10 and 100 fetal cells. Throughout this description, the concentration of fetal cells found in a freshly drawn maternal blood sample, prior to any further treatment, is referred to as the "naturally present concentration" of fetal cells, typically, but not necessarily, within the above ranges. Also throughout this description, the term "unenriched maternal blood" shall refer to a sample of maternal blood which contains only a naturally present concentration of fetal cells.

Since the naturally present concentration of fetal cells in unenriched maternal blood is so low, in order to obtain a diagnostically significant sample of fetal cells modern techniques include methods of physically isolating the fetal cells from the maternal cells in the sample. In essence, modern techniques are methods of concentrating the fetal cells within a sample, i.e., enriching the sample, for example by removing excess maternal cells, without removing fetal cells. These methods are extremely difficult to perform, often fail to isolate a sufficient number of fetal cells to be diagnostically significant and sometimes fail to provide a sample of a sufficient number of undamaged fetal cells of adequate purity for reliable subsequent diagnosis.

The normal human complement of chromosomes consists of the sex chromosomes (designated X and Y) and 22 autosomes (numbered 1-22). It has been estimated that a minimum of 1 in 10 human conceptions has a chromosome abnormality. As a general rule, an abnormal number of sex chromosomes is not lethal, although infertility can result. In contrast, an abnormal number of autosomes typically results in early death. Of the three autosomal trisomies found in live-born babies (trisomy 21, 18 and 13), only individuals with trisomy 21 (more commonly known as Down's syndrome), survive past infancy.

Although Down's syndrome is easily diagnosed after birth, prenatal diagnosis is problematic. To date, karyotyping of fetal cells remains the established method for the diagnosis of Down's syndrome and other genetic abnormalities associated with an aberration in chromosomal number and/or arrangement. Such genetic abnormalities include, for example, chromosomal additions, deletions, amplifications, translocations and rearrangements. The assessment of such abnormalities is made with respect to the chromosomes of a healthy individual, i.e., an individual having the above-described normal complement of human chromosomes.

Genetic abnormalities include the above-noted trisomies, such as Down's syndrome, as well as monosomies and disomies. Genetic abnormalities also include additions and/or deletions of whole chromosomes and/or chromosome segments. Alterations such as these have been reported to be present in many malignant tumors. Thus, aberrations in chromosome number and/or distribution (e.g., rearrangements, translocations) represent a major cause of mental retardation and malformation syndromes (du Manoir et al., et al., Human Genetics 90 (6): 590-610 (1993)) and possibly, oncogenesis. See also, e.g., (Harrison's Principles of Internal Medicine, 12th edition, ed. Wilson et al., McGraw Hill, N.Y., N.Y., pp. 24-46 (1991)), for a partial list of human genetic diseases that have been mapped to specific chromosomes, and in particular, for a list of X chromosome linked disorders. In view of the growing number of genetic disorders associated with chromosomal aberrations, various attempts have been reported in connection with developing simple, accurate, automated assays for genetic abnormality assessment.

In general, karyotyping is used to diagnose genetic abnormalities that are based upon additions, deletions, amplifications, translocations and rearrangements of an individual's nucleic acid. The "karyotype" refers to the number and structure of the chromosomes of an individual. Typically, the individual's karyotype is obtained by, for example, culturing the individual's peripheral blood lymphocytes until active cell proliferation occurs, preparing single, proliferating (e.g. metaphase, and possibly, interphase) cells for chromosome visualization, fixing the cells to a solid support and subjecting the fixed cells to in situ hybridization to specifically visualize discrete portions of the individual's chromosomes.

The rapid development of non-isotopic in situ hybridization techniques and the general availability of an ever-expanding repertoire of chromosome-specific DNA probes have extended the number of genetic disorders for which karyotyping is feasible. See, e.g., Lichter et al., "Analysis of Genes and Chromosomes by Non-isotopic in situ Hybridization", GATA 8(1):24-35 (1991). Such methods include the use of probe sets directed to chromosome painting for visualizing one or more preselected chromosomal subregions in a targeted fashion. Methods such as these require at least a modicum of knowledge regarding the types of aberration (s) expected in order to select useful DNA probes complementary to target nucleic acids present in a clinical or tumor cell sample.

Nucleic acid hybridization techniques are based upon the ability of a single stranded oligonucleotide probe to base-pair, i.e., hybridize, with a complementary nucleic acid strand. Exemplary in situ hybridization procedures are disclosed in U.S. Pat. No. 5,225,326 and copending U.S. patent application Ser. No. 07/668,751, the entire contents of which are incorporated herein by reference. Fluorescence in situ hybridization ("FISH") techniques, in which the nucleic acid probes are labeled with a fluorophor (i.e., a fluorescent tag or label that fluoresces when excited with light of a particular wavelength), represents a powerful tool for the analysis of numerical, as well as structural aberrations chromosomal aberrations. See, e.g., PCT Application WO 94/02646, inventors M. Asgari et al., published Feb. 3, 1994, hereinafter, "Asgari") co-pending U.S. patent application Ser. No. 07/915,965; P. Lichter, et al., Genet. Anal. Tech. Appl. 8: 24-35 (1991); and S. Du Manoir, et al., Human Genetics 90 (6): 590-610 (1993), the entire contents of which publications are incorporated herein by reference.

Asgari reports in situ hybridization assays for determining the sex of a fetus, genetic characteristics or abnormalities, infectious agents and the like, by nucleic acid hybridization of fetal cells such as those circulating in material blood. The fetal cells are distinguished from maternal cells present in the fixed sample by staining with an antibody which specifically recognizes the maternal or fetal cell or by in situ hybridization to detect one or more fetal mRNAs. The method reportedly is useful for detecting chromosomal abnormalities in fetal cells. However, the fetal cells must be enriched prior to analysis.

PCT Application WO 94/02830, inventors M. Greaves, et al., published Feb. 3, 1994, (hereinafter, "Greaves") report a method for phenotyping and genotyping a cell sample. The method involves contacting a fixed cell with an antibody labeled with a first fluorophor for phenotyping the cell via histochemical staining, followed by contacting the fixed cell with a DNA probe labeled with a second fluorophor for genotyping the cell. The first and second fluorophors fluoresce at different wavelengths from one another, thereby allowing the phenotypic and genetic analysis on the identical fixed sample.

Despite the above-described advances in the development of fluorescent in situ hybridization methods for the diagnosis of genetic abnormalities, the analysis of the fluorophor-labeled sample remains labor-intensive and involves a significant level of subjectivity. This is particularly true in connection with the prenatal diagnosis of genetic abnormalities in which fetal cells must either be isolated from maternal cells or visually distinguished therefrom prior to assessment for genetic abnormalities. Thus, for example, a laboratory technician must manually prepare and sequentially stain the sample (first, with a histochemical stain to phenotype the cells, second, with a hybridization probe to genotype the cell); visually select fetal cells from other cells in the optical field (using, for example, the above-mentioned histochemical staining procedure); assess the relative distribution of fluorescent color that is attributable to hybridization of the fluorophor-tagged probe; and compare the visually-perceived distribution to that observed in control samples containing a normal human chromosome complement. As will be readily apparent, the above-described procedure is quite time-consuming. Moreover, because the results are visually-perceived, the frequency of erroneous results can vary from one experiment to the next, as well as from one observer to the next.

The discussion thus far has focused on a particular type of rare cell, fetal cells circulating in the mother's peripheral blood, and a particular diagnostic setting, detecting trisomy 21 (Down's syndrome). Many other diagnostic settings are known in which a signal is to be detected in other rare cells. For example, a particular enzyme level or genetic characteristic found in cells of a particular morphology may indicate a condition of medical significance, such as a precancerous condition, a cancerous tumor, a metastasis of a tumor, infection by a virus, and various other genetic conditions, for example.

3. SUMMARY OF THE INVENTION

It is desired to provide a computer controlled method and apparatus for detecting and diagnosing a rare cell type in a tissue sample, said diagnosis being based upon a characteristic of that rare cell. It is further desired to provide a computer controlled method and apparatus for detecting fetal cells in a blood preparation and performing a fetal cell based prenatal diagnosis that solves the above-identified problems, which overcomes such other problems and meets such other goals as will be apparent to the person skilled in this art after reading a description of the invention. It is also desired to provide a computer implemented diagnostic screen for genetic disorders.

The invention in one aspect involves a method of operating a computer system to detect whether a genetic condition defined by at least one target nucleic acid is present in a sample. The method involves the use of probes and digitized images of the probes hybridized to a sample, together with counting objects and analysis of a statistical expectation to detect whether the genetic condition is present. The counting may involve, for example, counting the number of times a genetic abnormality is detected and comparing that count to a statistical expectation of the abnormality in a particular tissue type, cell type or sample. The counting may involve counting the number of times a genetic abnormality occurs and comparing that count to the number of times a cell type occurs in the same sample or to the number of times a normal nucleic acid occurs in the same sample. The counting may involve counting the number of times more than one different genetic abnormality occurs in a single cell. The computer system also may be used to identify cell type, count cells, examine cell morphology, etc. and compare or correlate this information with the count of the genetic abnormality. Various diagnostic circumstances are described below and are known to those of ordinary skill in the art.

One method of counting involves fluorescence in situ hybridization. This aspect of the invention, which is preferred, is exemplary of the methods of the invention.

Generally, the invention provides a method of operating a computer system to detect whether a genetic condition defined by at least one target nucleic acid is present in a fixed sample, the method comprising: receiving a digitized image, preferably a color image, of the fixed sample, which has been subjected to fluorescence in situ hybridization under conditions to specifically hybridize a fluorophor-labeled probe to the target nucleic acid; processing the color image in a computer to separate objects of interest from background; measuring size and color parameters of the objects of interest; identifying first objects having specific predetermined characteristics associated with the target nucleic acid; counting first objects identified; and analyzing the count of first objects with respect to a statistical expectation to detect whether the genetic condition is present. This method is applicable to many genetic conditions, including wherein the genetic condition is human trisomy 21. In addition to the foregoing, it will be understood that the statistical expectation can be based on a tissue type, for example. The computer can be used to identify the tissue type of a cell being examined, but the tissue type also can be known.

In some embodiments, the step of receiving further includes a step of producing an image file of red, green and blue pixels representative of red, green and blue intensities at respective pixel locations within the color image received. In some embodiments, the step of processing further includes steps of manually selecting a plurality of pixels within the background; determining color intensity value ranges corresponding to the portion of the background; and identifying as the background those areas of the image having color intensity values within the ranges determined. In some embodiments, before the step of measuring, there may be processing in the computer to filter the color image to make color intensity values of dark pixels in the color image lighter and to make color intensity values of light pixels in the color image darker. The step of filtering may further comprise passing the color image through a hole filling filter; passing the filled color image through an erosion filter; performing a separate operation on the eroded filled color image, to define outlines around areas; selecting pixels within the outlines by performing a logical NOT operation; and performing a logical AND operation between the selected pixels and the filled color image.

In some embodiments, the genetic condition is further defined by a ratio of the target nucleic acid to a second nucleic acid. Then, the method further includes identifying second objects having specific predetermined characteristics associated with the second nucleic acid; and counting second objects identified; wherein analyzing the count of first objects includes finding a ratio of the count of first objects to the count of second objects. In some embodiments, the target nucleic acid defines a dominant trait and the second nucleic acid defines a corresponding recessive trait. The method in those embodiments may include indicating the genetic condition as possessing the dominant trait, possessing the recessive trait, or possessing the dominant trait and carrying the recessive trait depending on the ratio found. When the target nucleic acid is a rearrangement of the second nucleic acid, the method may further include selecting the probe to hybridize with a break region between rearranged and non-rearranged nucleic acids. Finally, the method may include indicating the genetic condition as a severity level related to the ratio found.

According to the invention, instructions for carrying out the above methods may be recorded on a computer medium. The invention may then provide a computer software product comprising: a computer readable storage medium having fixed therein a sequence of computer instructions directing a computer system to detect whether a genetic abnormality is present in a fixed sample containing at least one target nucleic acid, the instructions directing steps of: receiving a digitized color image of the fixed sample, which has been subjected to fluorescence in situ hybridization under conditions to specifically hybridize a fluorophor-labeled probe to the target nucleic acid; processing the color image in a computer to separate objects of interest from background; measuring size and color parameters of the objects of interest so as to identify and enumerate objects having specific predetermined characteristics associated with the target nucleic acid; and analyzing the enumeration of objects with respect to a statistically expected enumeration to detect whether the genetic abnormality is present. The steps defined by the instructions recorded on the medium may be varied as described above in connection with the method.

A method of operating a computer according to yet another aspect of the invention to count occurrences of a target substance in a cell-containing sample which has been labeled with a target-specific fluorophor may comprise: receiving a digitized color image of the fluorophor-labeled sample; obtaining a color image of the fluorophor-labeled sample; separating objects of interest from background in the color image; measuring parameters of the objects of interest so as to enumerate object having specific characteristics; and analyzing the enumeration of objects with respect to a statistically expected enumeration to determine the genetic abnormality. Again, the steps of the method may be varied as above.

Similarly, there is, according to other aspects of the invention, a computer software product comprising: a computer readable storage medium having fixed therein a sequence of computer instructions directing a computer system to count occurrences of a target substance in a cell-containing sample which has been labeled with a target-specific fluorophor, the instructions directing steps of: receiving a digitized color image of the fluorophor-labeled sample; obtaining a color image of the fluorophor-labeled sample; separating objects of interest from background in the color image; measuring parameters of the objects of interest so as to enumerate object having specific characteristics; and analyzing the enumeration of objects with respect to a statistically expected enumeration to determine the genetic abnormality. The instructions can be made to implement all of the variations on the methods described above.

According to yet another aspect of the invention, there is provided an apparatus for analyzing an image of a cell-containing sample which has been labeled with a target-specific fluorophor, comprising: a computer system on which image processing software executes; and a storage medium in which is fixed a sequence of image processing instructions including receiving a digitized color image of the fluorophor-labeled sample, obtaining a color image of the fluorophor-labeled sample, separating objects of interest from background in the color image, measuring parameters of the objects of interest so as to enumerate object having specific characteristics, and analyzing the enumeration of objects with respect to a statistically expected enumeration to determine the genetic abnormality. Again, the instructions can be varied to implement all the variations described above.

In yet another aspect, the invention provides a computer-implemented method of processing body fluid or tissue sample image data, the method comprising creating a subset of a first image data set representing an image of a body fluid or tissue sample taken at a first magnification, the subset representing a candidate blob which may contain a rare cell creating a subset of a second image data set representing an image of the candidate blob taken at a second magnification, the subset of the second data set representing the rare cell, storing the subset of the second data set in a computer memory, measuring size and color parameters of the objects of interest so as to identify objects having specific predetermined characteristics associated with the target nucleic acid, counting the objects identified in the step of measuring, and analyzing the count of objects with respect to a statistically expected count to detect whether the genetic abnormality is present.

In general, a subset of a first image data set can be created by observing an optical field of a monolayer of cells from a body fluid or tissue sample using a computerized microscopic vision system to detect a signal indicative of the presence of a rare cell.

The method can further produce an image file of red, green and blue pixels representative of red, green and blue intensities at respective pixel locations within the color image received. According to some aspects of the invention, the processing further includes manually selecting a plurality of pixels within the background; determining color intensity value ranges corresponding to the portion of the background; and identifying as the background those areas of the image having color intensity values within the ranges determined. The method may include before the step of measuring, processing in the computer to filter the color image to make color intensity values of dark pixels in the color image lighter and to make color intensity values of light pixels in the color image darker. Moreover, the filtering may include passing the color image through a hole filling filter; passing the filled color image through an erosion filter; performing a separate operation on the eroded filled color image, to define outlines around areas; selecting pixels within the outlines by performing a logical NOT operation, and performing a logical AND operation between the selected pixels and the filled color image.

The method further comprises contacting a body fluid or tissue sample at a location corresponding to each candidate blob represented in the subset of the first image data set, with a reagent to generate a medically significant signal. This method provides the advantage of being able to remove from further processing a body fluid or tissue sample for which no subset of the first data set representing a candidate blob is created. The signal can be measured to determine whether it is a significant signal level. The first and/or the second image data subsets can be transformed into a representation that is more suitable for control and processing by a computer as described herein. In a preferred embodiment, the image data is transformed from an RGB (Red Green Blue) signal into an HLS (Hue Luminescence Saturation) signal. Filters and/or masks are utilized to distinguish those cells that meet preselected criteria and eliminate those that do not, and thus identify rare cells.

In another aspect of the invention, there is provided a method of operating a laboratory service, the method comprising steps of receiving a body fluid or tissue sample, creating a body fluid or tissue sample smear, operating a computerized microscope so that a software program automatically identifies a rare cell in the smear and detecting a medically significant signal in the rare cell.

In yet another aspect of the invention, there is provided computer software product including a computer-readable storage medium having fixed therein a sequence of instructions which when executed by a computer direct performance of steps of detecting and diagnosing a rare cell type. The steps encompass: creating a subset of a first image data set representing an image of a body fluid or tissue sample taken at a first magnification, the subset representing a candidate blob which may contain a rare cell creating a subset of a second image data set representing an image of the candidate blob taken at a second magnification, the subset of the second data set representing the rare cell, storing the subset of the second data set in a computer memory, measuring size and color parameters of the objects of interest so as to identify objects having specific predetermined characteristics associated with the target nucleic acid; counting the objects identified in the step of measuring; and analyzing the count of objects with respect to a statistically expected count to detect whether the genetic abnormality is present.

In general, a subset of a first image data set can be created as described above. The method can further produce an image file of red, green and blue pixels representative of red, green and blue intensities at respective pixel locations within the color image received. According to some aspects of the invention, the processing further includes manually selecting a plurality of pixels within the background; determining color intensity value ranges corresponding to the portion of the background; and identifying as the background those areas of the image having color intensity values within the ranges determined. The method may include before the step of measuring, processing in the computer to filter the color image to make color intensity values of dark pixels in the color image lighter and to make color intensity values of light pixels in the color image darker. Moreover, the filtering may include passing the color image through a hole filling filter; passing the filled color image through an erosion filter; performing a separate operation on the eroded filled color image, to define outlines around areas; selecting pixels within the outlines by performing a logical NOT operation, and performing a logical AND operation between the selected pixels and the filled color image. The steps further encompass contacting a body fluid or tissue sample at a location corresponding to each candidate blob represented in the subset of the first image data set, with a reagent to generate a medically significant signal. This provides the advantage of being able to remove from further processing a body fluid or tissue sample for which no subset of the first data set representing a candidate blob is created. There is an optional step by which the signal can be measured to determine whether it is of a significant level. Another optional step encompasses transformation of one or both of the first and the second image data subsets into a representation that is more suitable for control and processing by a computer as described herein. In a preferred embodiment, the image data is transformed from an RGB (Red Green Blue) signal into an HLS (Hue Luminescence Saturation) signal. Filters and/or masks are utilized to distinguish those cells that meet pre-selected criteria and eliminate those that do not.

According to one aspect of the invention, there is provided a method of preparing a sample of cells for a diagnostic procedure. The sample of cells is obtained and fixed as a monolayer on a substrate, the sample of cells including a rare cell which is present in the sample at no greater than one in every 10,000 cells (i.e. no greater than 0.01%). An optical field covering at least a portion of the sample of cells is observed using a computerized microscopic vision system for a signal indicative of the presence of a rare cell. The signal is detected, and coordinates where the signal is detected are identified, for the diagnostic procedure. In one embodiment the rare cell is present at no greater than 0.001% of the cells. In other embodiments the rare cell is present at no greater than 0.0001%, 0.00001% or even 0.000001%.

In one particularly important embodiment, the rare cell is a fetal cell in a sample of cells from maternal blood. In a preferred embodiment, the sample contains only a naturally present concentration of fetal cells which can be no greater than 0.001%, 0.0001%, 0.00001%, 0.000001% or even 0.0000001%.

In another specific embodiment of the invention, the rare cell type to be detected and diagnosed is a cancer cell found in a sample of cells or tissue from an animal or patient. The sample can be blood or other body fluid containing cells or a tissue biopsy. As an illustration of this embodiment, cancer cell markers described in Section 5, infia, e.g, GM4 protein, telomerase protein or nucleic acids, and p53 proteins or nucleic acids, may be used in the generation of the first or second signal, in a manner to be determined by the specific application of the invention.

In one embodiment of the invention, when the rare cell type is present in the sample, the method of the invention detects the rare cell type at a frequency of no less than 80%. In other embodiments, the detection frequencies are no less than 85%, 90%, 95% and 99%.

According to one particularly important embodiment of the invention, there is provided a method of preparing a sample of blood for a diagnostic procedure, which includes: preparing a smear of a sample of unenriched maternal blood containing a naturally present concentration of fetal cells; observing an optical field covering a portion of the smear using a computerized microscopic vision system for a signal indicative of the presence of a fetal cell; detecting said signal; and identifying, for the diagnostic procedure, coordinates within the smear at which the signal is detected.

In one embodiment, the signal is further processed to represent morphological measurements of the rare cell. In another embodiment, the cells are treated with a label to enhance the optical distinction of rare cells from other cells. In this embodiment, the signal can be, for example, from a label which selectively binds to the rare cells. In another embodiment, the diagnostic procedure involves moving to the coordinates identified and magnifying the optical field until the image is of an isolated rare cell.

In some embodiments, the optical field is stepped over a sequence of portions of the cells covering substantially all of the cells. This may be achieved, for example, by moving the cells on the substrate under control of the computerized microscopic vision system relative to a lens of the computerized microscopic vision system. In another embodiment, the coordinates at which the first signal was obtained are identified, and then the rare cell at those coordinates specifically is contacted after the coordinates have been identified.

According to another aspect of the invention, there is provided a method of obtaining from a sample of cells a signal having diagnostic significance relative to a rare cell in the sample of cells. The rare cell is present in the sample at no greater than one in every 10,000 cells. The method includes preparing a monolayer of the sample of cells fixed on a substrate. The rare cell is contacted with an agent to generate a diagnostic signal, the diagnostic signal having the diagnostic significance. The monolayer is observed using a computerized microscopic vision system to obtain the diagnostic signal. In some embodiments, the diagnostic signal can be used to identify the rare cell. In other embodiments, a locating signal can be used to identify the rare cell, and the diagnostic signal is obtained after the cell is located.

In one embodiment, the rare cell is present in the sample at no greater than one in every 10,000 cells (i.e., no greater than 0.01% of the cells). In other embodiments, the rare cell is present at no greater than 0.001%, 0.00001% or even 0.000001%. In one particularly important embodiment, the rare cell is a fetal cell in a sample of cells from maternal blood. Preferably the sample contains only a naturally present concentration of fetal cells which can be no greater than 0.001%, 0.0001%, 0.00001%, 0.000001% or even 0.0000001%.

According to an important embodiment of the invention, there is provided a method of obtaining from a sample of unenriched maternal blood, containing a naturally present concentration of fetal cells, a signal having diagnostic significance relative to the fetal cells. The method includes: preparing a smear of the sample of unenriched maternal blood; observing the smear using a computerized microscopic vision system to obtain a first signal indicative of the presence of a fetal cell; contacting the fetal cell with an agent to generate a second signal, the second signal having the diagnostic significance; and observing the fetal cell using the computerized microscopic vision system to obtain the second signal. In one embodiment, the smear can comprise at least 250 µl of the unenriched maternal blood and even can comprise at least 500 µl of the unenriched blood.

As described above, the first signal can be further processed to represent morphological measurements of the rare cell. Likewise, the cells can be treated with a label to enhance optical distinctions of rare cells from other cells, such as maternal cells. To achieve this, the first signal can be from a label which selectively binds to the rare cell, such as a fetal cell. Likewise, as above, the step of observing can involve stepping an optical field over a sequence of portions of the cells, which can be accomplished, for example, by moving the cells or the substrate under control of the computerized microscopic vision system relative to a lens of the computerized microscopic vision system.

In any of the foregoing embodiments, the cells can be prepared on a substrate, and a coordinate system can be calibrated to the substrate so that coordinates of the rare cell identified in one step can be returned to later in another step. Likewise, the substrate in certain important embodiments has a length that is 10 times its width, the substrate being substantially elongated in one direction. The length can even be 20 times the width. The substrate can be a flexible film, and in one important embodiment, is an elongated flexible film that can carry a relatively large volume of cells, such as would be provided from a relatively large volume of smeared maternal blood.

In any of the foregoing embodiments, the first signal and the second signal can be selected whereby they do not mask one another when both are present. Likewise, in any of the foregoing embodiments, the second signal can be generated by in situ PCR or PCR in situ or fluorescence in situ hybridization (FISH). Alternatively, in a particularly preferred embodiment, in any of the foregoing embodiments, the second signal can be generated by rolling-circle amplification (RCA). RCA generates a single stranded DNA (ssDNA) comprising tandem repeats of a target gene sequence. In a specific mode of signal generation using RCA, one or a combination of detectable labels, such as fluorophores useful for multi-parametric are coupled to nucleic acid probes complementary to the ssDNA generated by RCA color coding are used in an RCA format designated "condensation of amplified circles after hybridization of encoding tags" (RCA-CACHET). In another mode of signal generation using RCA, a hapten is incorporated into the ssDNA and detected by means of immunocytochemistry.

In an alternative embodiment, the first step of the process is performed using fluorescence microscopy, which enables identification of the possible rare cell positions at even lower magnification and higher processing speed compared with the method described above. The rare cells of interest are stained with a fluorescent label or fluorophore.

In one important embodiment, the substrate is a plurality of substrates on which the sample of cells is prepared, such as a plurality of smears of maternal blood, each of the plurality including a total of at least 5 µl of the.sample. A rare cell-containing substrate (in which the first signal is obtained) is identified. Then, only the rare cell-containing substrate/substrates which has/have been identified is/are treated to generate the second signal.

According to yet another aspect of the invention, there is provided a method of performing a diagnosis for a fetus, using an unenriched sample of maternal blood containing naturally present fetal cells. This method includes: preparing a smear of at least 250 µl of the sample of unenriched maternal blood; identifying a fetal cell within the smear; contacting the fetal cell with an agent that produces a diagnostic signal; and observing the diagnostic signal. In one important embodiment, the step of identifying can comprise observing cells within the smear, using a computerized microscopic vision system, measuring a signal produced by the observed cells indicative of the presence of fetal cells, and defining coordinates at which the measured signal indicates the presence of the fetal cell. Important embodiments directed to volumes of the maternal blood, substrate configurations and so forth are as described above.

According to yet another aspect of the invention, there is provided a method of obtaining from a sample of unenriched maternal blood containing a naturally present concentration of fetal cells, an image of a substantially isolated fetal cell. This method includes: preparing a smear of at least 250 µl of the sample of unenriched maternal blood; observing the smear with a computerized microscopic vision system for a signal indicative of the presence of a fetal cell; identifying coordinates at which the signal is observed; moving to the coordinates identified, an optical field including an image of the fetal cell; and magnifying the optical field until the image is of an isolated fetal cell. Important embodiments directed to volumes of the maternal blood sample, substrate configurations and so forth are as described above.

According to yet another aspect of the invention, there is provided a device for screening fetal cells contained within a smear of an unenriched sample of maternal blood containing a naturally present concentration of fetal cells, comprising: a flexible film having thereon a smear of at least 250 µl of maternal blood. In one embodiment, the flexible film has thereon a smear of at least 500 µl of maternal blood. In one important embodiment, the flexible film is an elongated film, the length being at least 10 times the width. It is particularly preferred that the flexible film include marking coordinates, whereby the computerized microscopic vision system described herein can locate a cell relative to a point on the film, permitting that cell to be returned to at a later time, if desired.

According to yet another aspect of the invention, there is provided a device for screening rare cells contained within a sample of cells at a concentration of no greater than one rare cell for every 10,000 cells in the sample of cells. The device is a flexible film having fixed thereon the sample of cells, wherein the flexible film is at least five inches long. In one preferred embodiment the flexible film has a length at least 10 times its width. In another important embodiment, the flexible film includes marking coordinates, whereby the computerized microscopic vision system described herein can locate a cell relative to a point on the film, permitting the cell to be returned to at a later time, if desired.

According to another aspect of the invention, there is provided a device for dispensing materials to a specific location on a slide. The device includes a microscopic vision system for detecting a signal indicative of the presence of a rare cell in a sample of cells. The device also includes means for identifying the coordinates of the rare cell in an optical field. The device further has attached to it a dispenser for dispensing a volume of material and means for moving the dispenser to the coordinates whereby the volume of material may be dispensed upon the rare cell. The material dispensed can be reagents such as a label, PCR, primers, and the like. According to another important embodiment of the invention, the need for scanning large areas of microscopic preparations in the minimum possible amount of time is met by the use of an apparatus or system that provides a "composed" image. It is based on the simultaneous use of an array of computer controlled objective lenses, arranged on a support system and having the capacity to focus on a microscopic preparation. Each of the objective lenses is connected to a charge coupled device camera, herein referred to as a CCD camera, being connected to image acquisition hardware installed in a host computer. The images are stored in the computer memory and they are combined in an appropriate side to side fashion, so that a "composed" image is formed in the computer memory. The "composed" image can be further processed as a unity, using any kind of imaging procedures to detect specific features that are in question. The significant advantage of the described system consists in its capacity to acquire images simultaneously from a number of objective lenses, thus minimizing the time needed to process large areas of the sample in a manner that is inversely proportional to the number of objectives used.

The "composing" system can process any kind of microscopic preparation using either transmitted or reflected light. It is particularly useful where large numbers of samples need to be processed imposing significant time constraints, for example, for processing large numbers of microscopic biological preparations for screening and/or diagnostic purposes, etc.

4. BRIEF DESCRIPTION OF THE DRAWINGS

In the accompanying drawings, in which like reference designations indicate like elements:

Figure 4A:
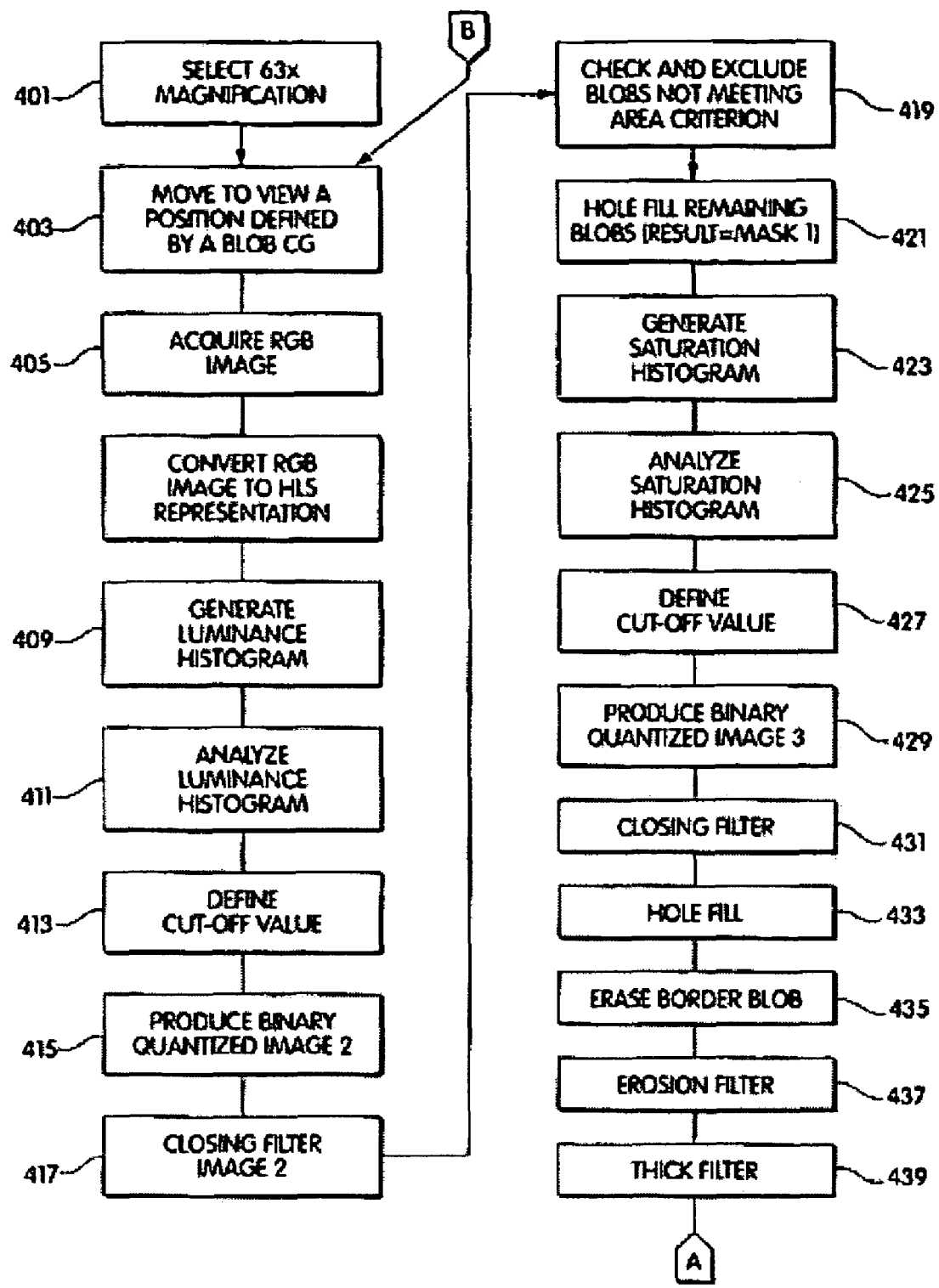
Figure 4B:
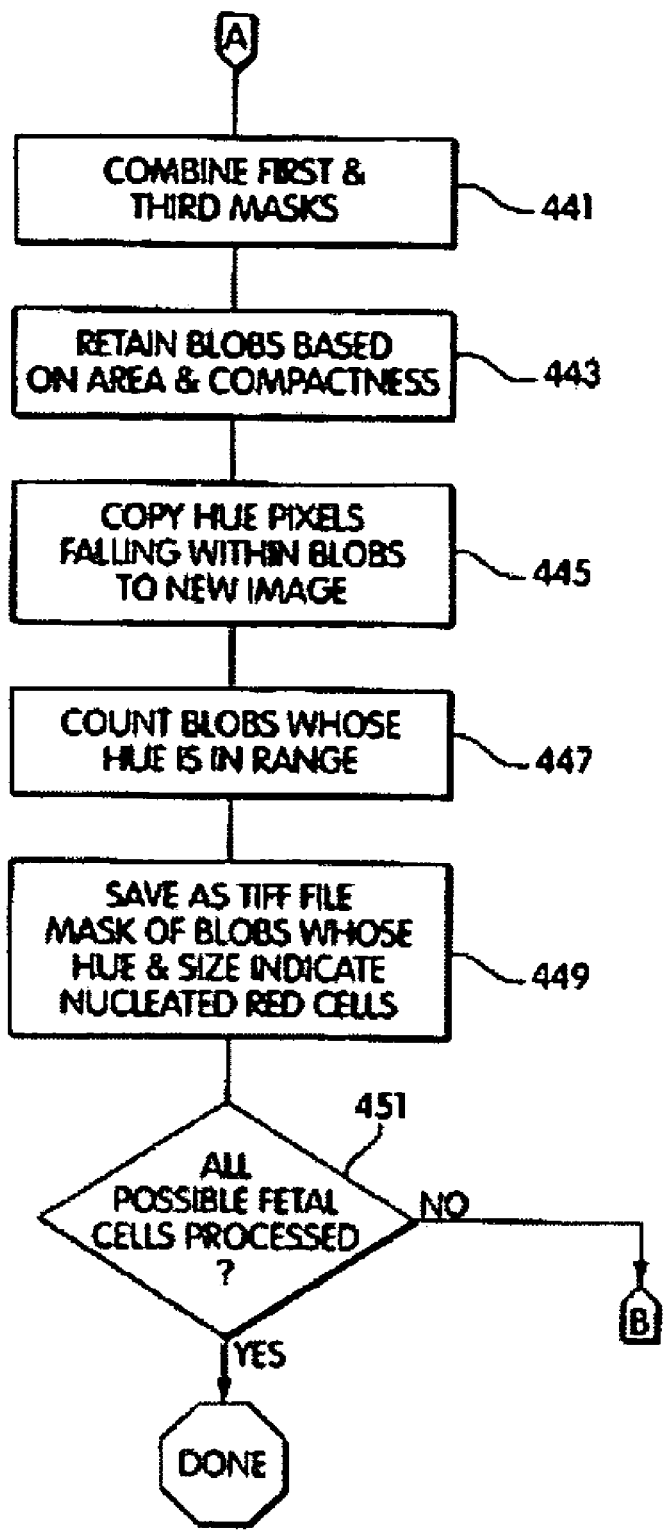
Figure 5:
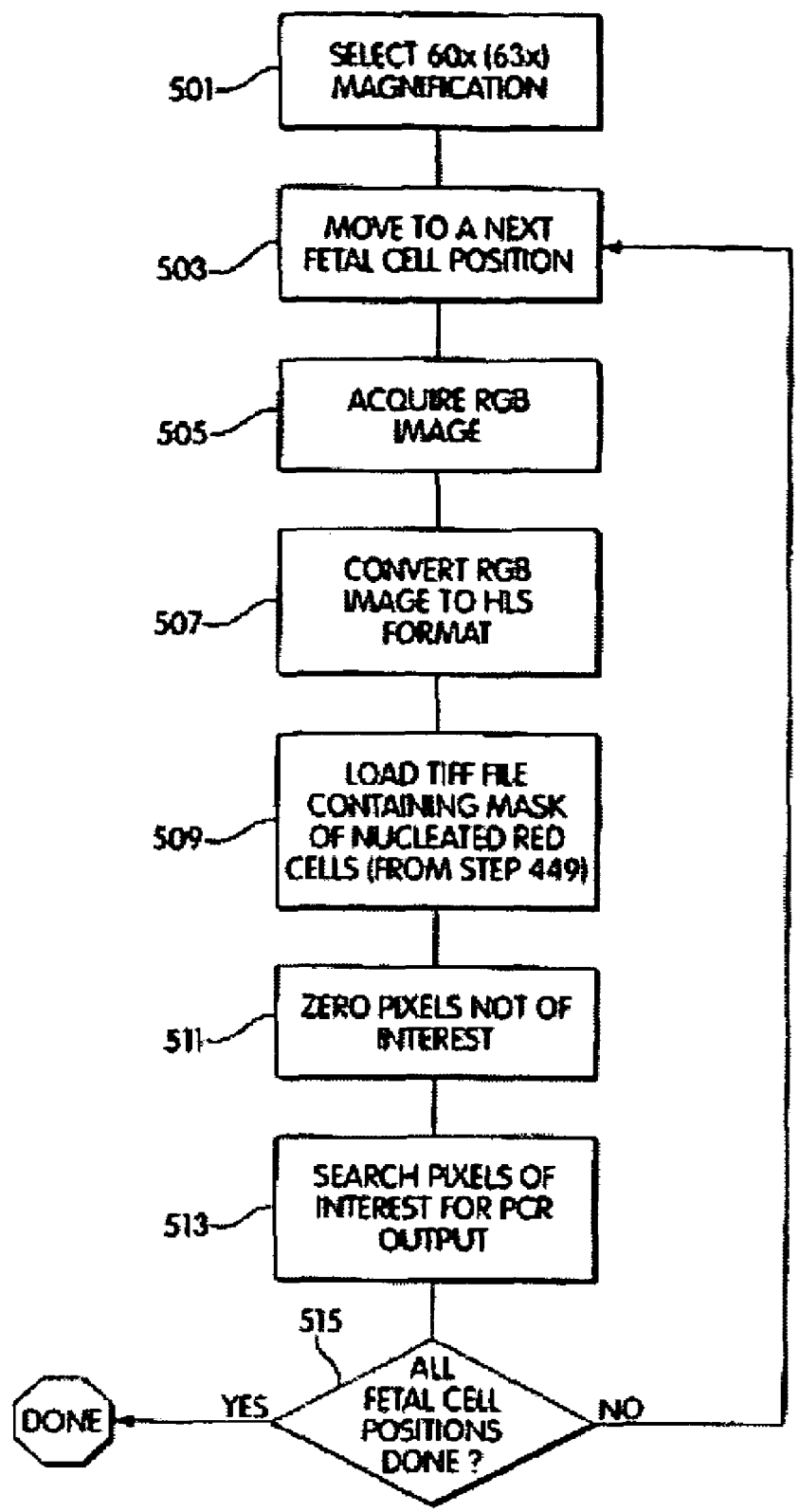
Figure 6:
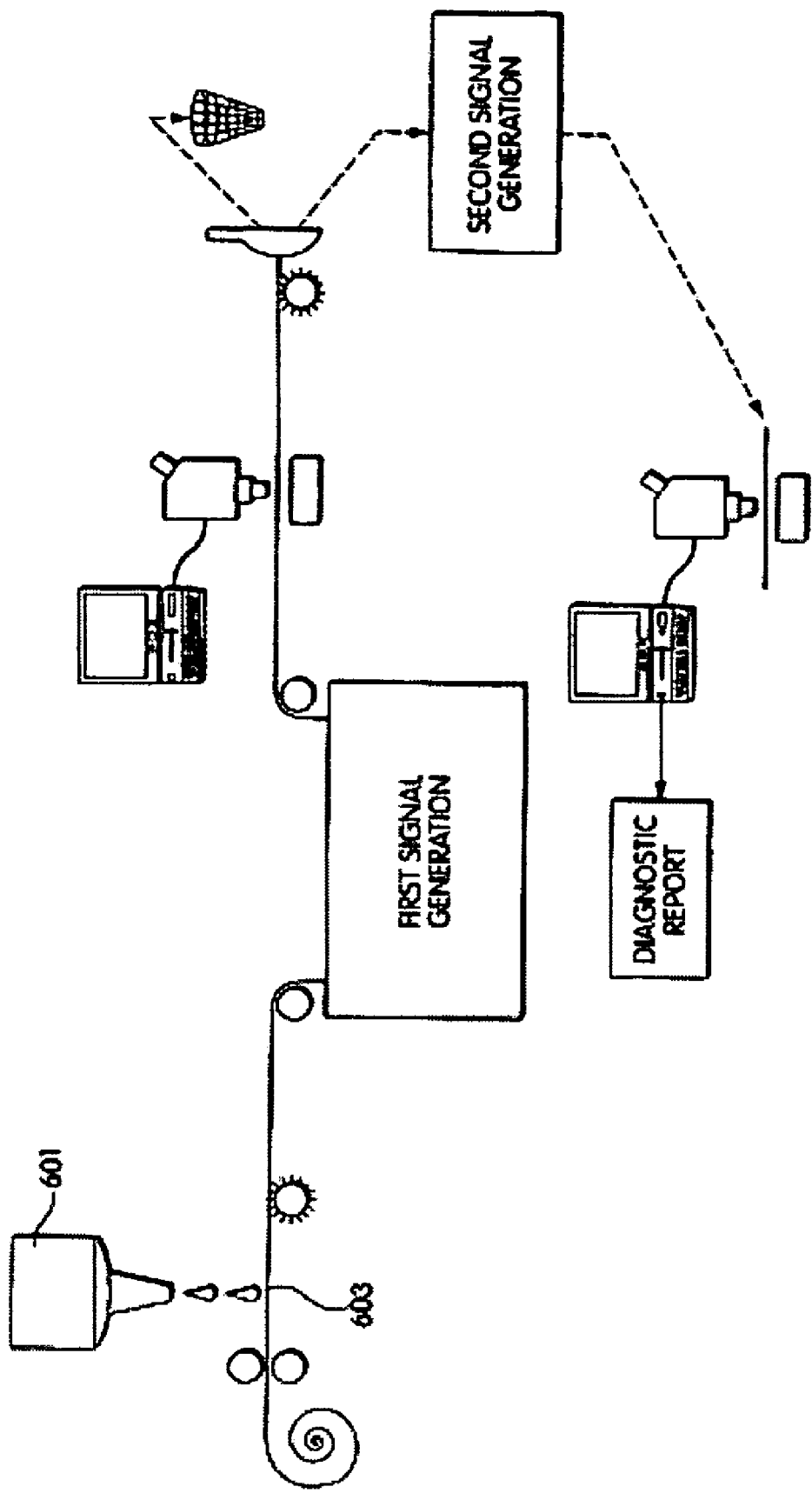
Figure 7:
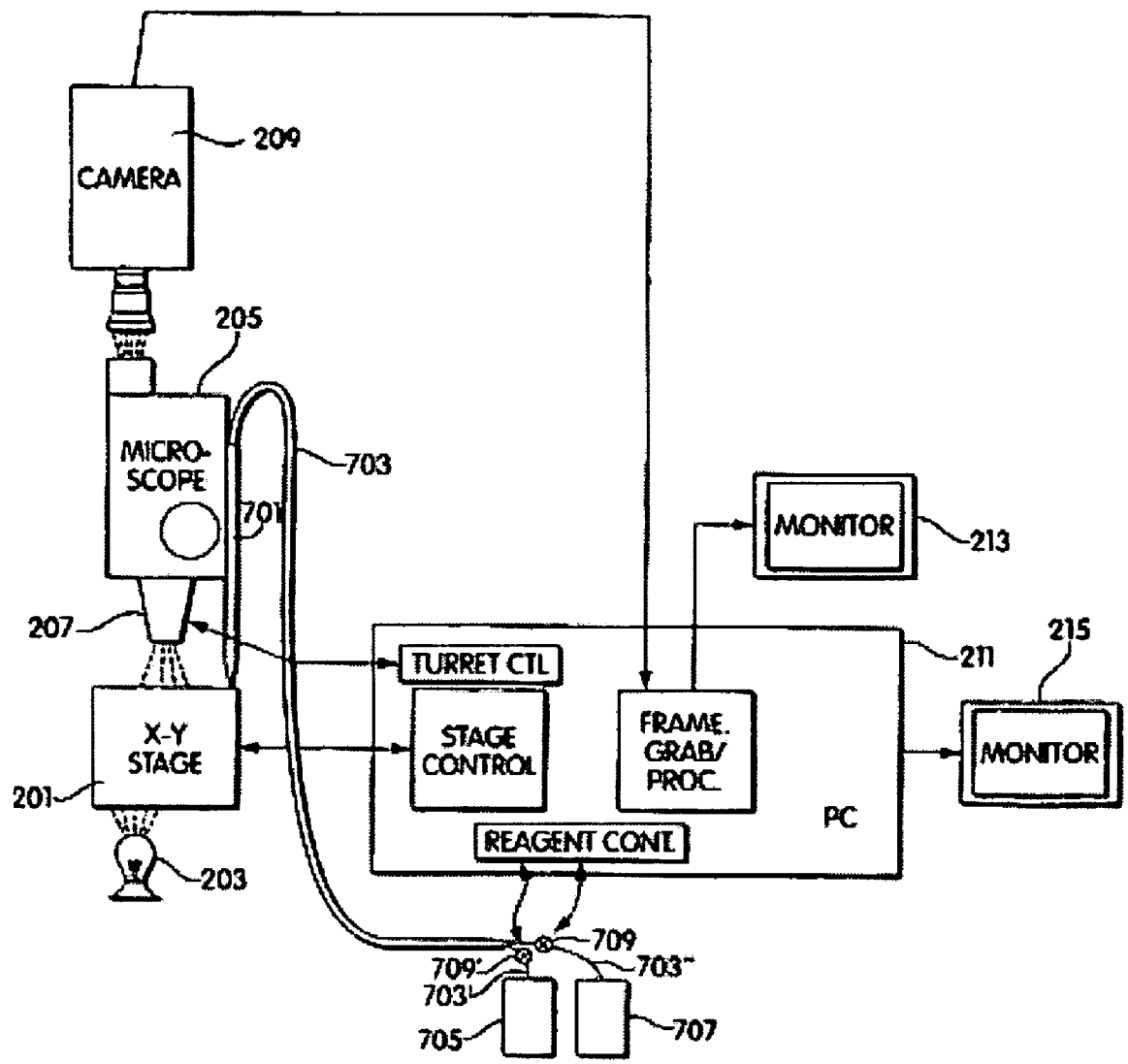
Figure 8:
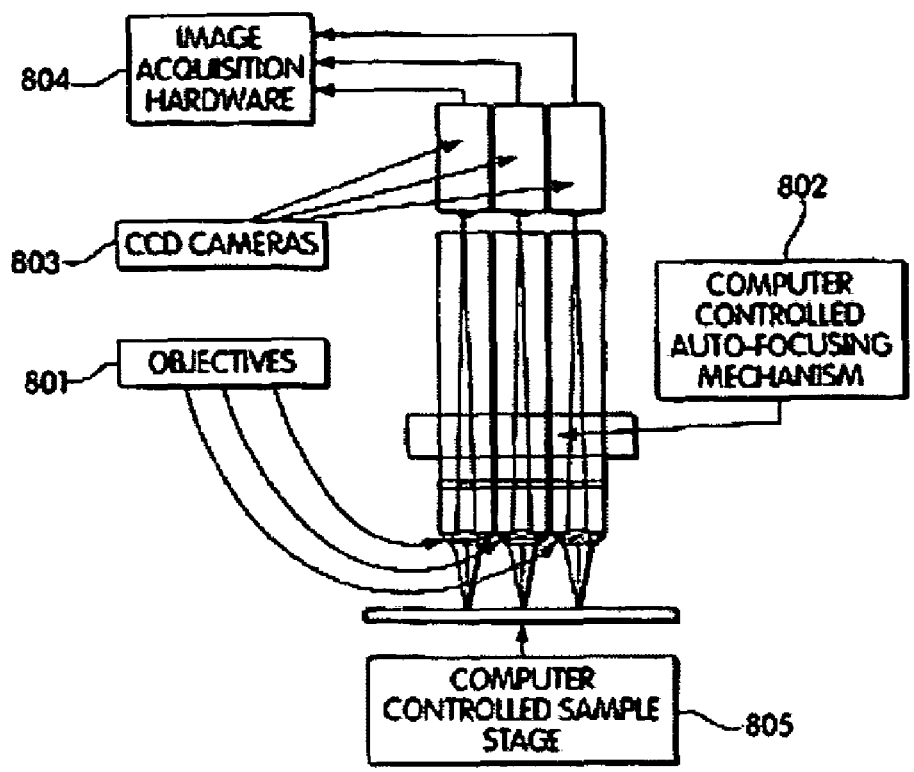
Figure 9:
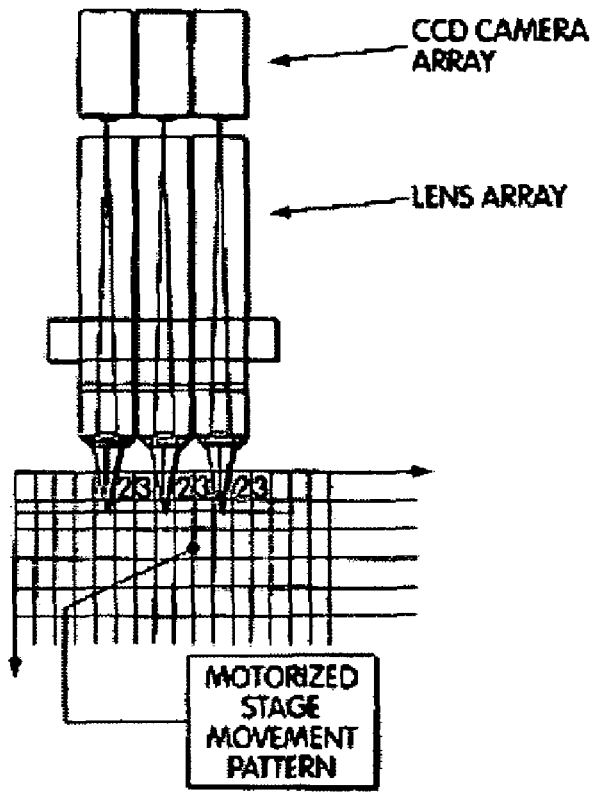
Figure 10:
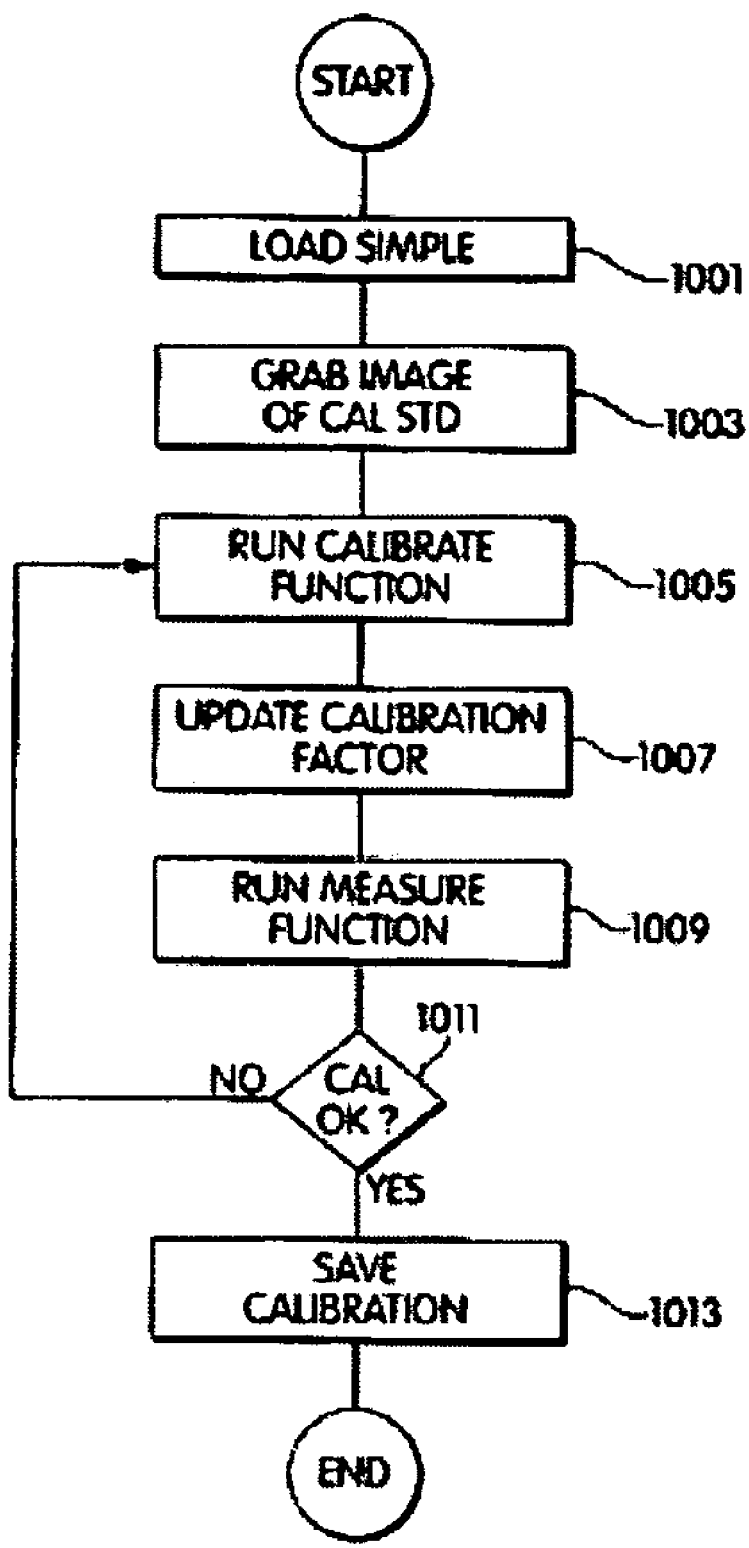
Figure 11:
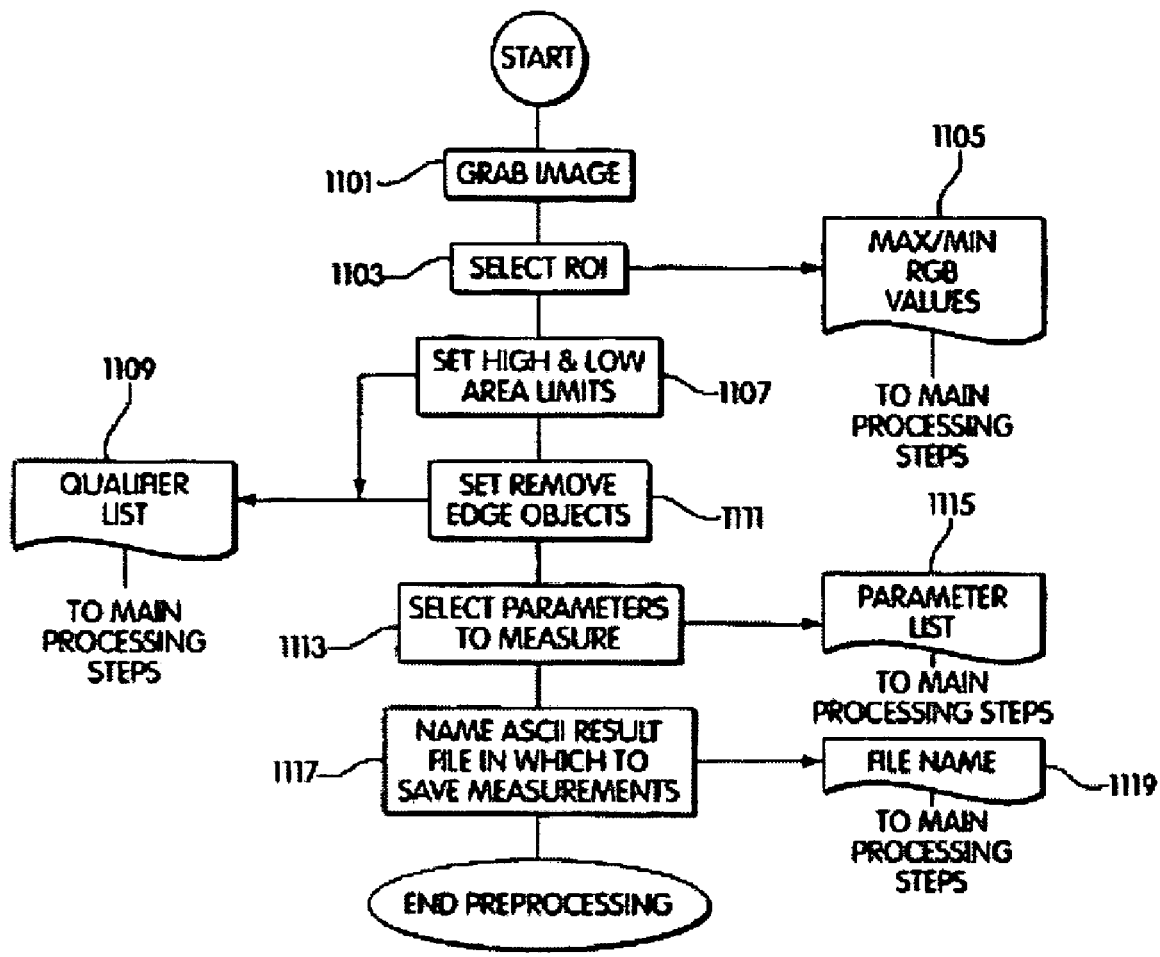
Figure 12A:
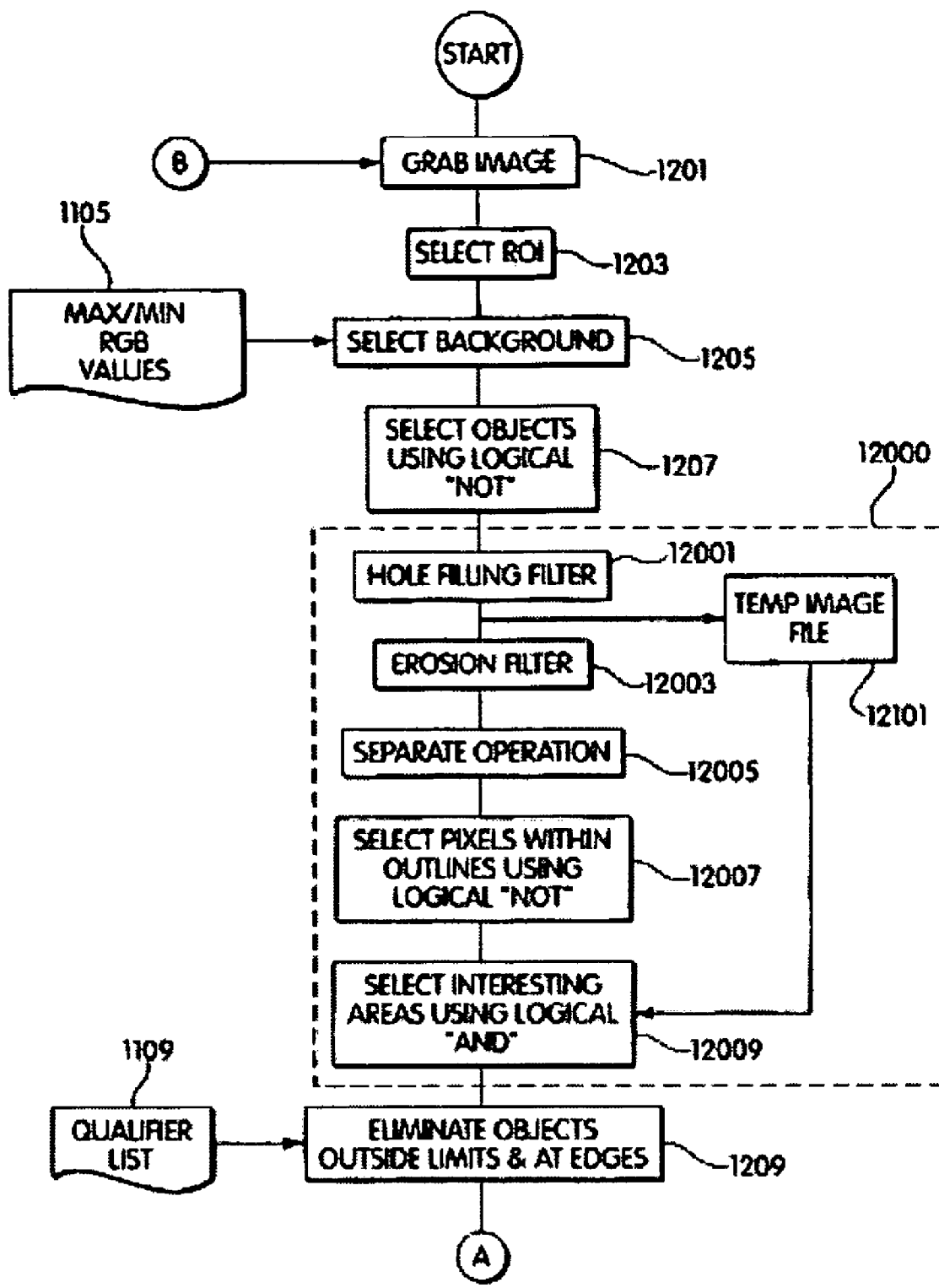
Figure 12B:
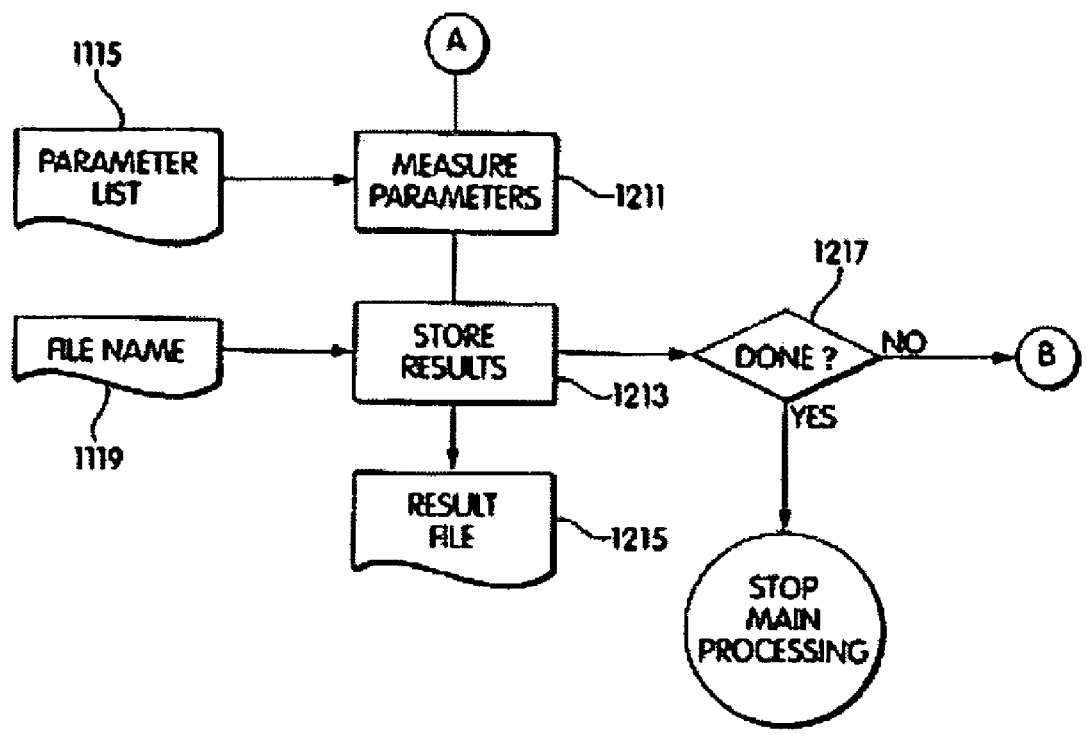

FIGS. 4A and 4B taken together are a flow chart of stage II leading to detecting the first signal;

FIG. 5 is a flow chart of detection of the second signal;

FIG. 6 is a schematic representation of a variation of an apparatus embodying aspects of the invention, using a continuous smear technique;

FIG. 7 is a block diagram of an analysis and reagent dispensing system used in one embodiment of one aspect of the invention;

FIG. 8 is an outline of a multiple objective microscopy system;

FIG. 9 is an image "composition" method;

FIG. 10 is a flowchart of the calibration steps of one embodiment of the invention;

FIG. 11 is a flowchart of the preprocessing steps of one embodiment of the invention; and FIGS. 12A and 12B are a flowchart of the main processing steps of one embodiment of the invention.

5. DETAILED DESCRIPTION OF THE INVENTION

The invention will be better understood upon reading the following detailed description of the invention and of various exemplary embodiments of the invention, in connection with the accompanying drawings. While the detailed description explains the invention with respect to fetal cells, a rare cell type, and blood as the body fluid or tissue sample, it will be clear to those skilled in the art that the invention can be applied to and, in fact, encompasses diagnosis based on any cell type and any body fluid or tissue sample for which it is possible to create a monolayer of cells on a substrate.

Body fluids and tissue samples that fall within the scope of the invention include but are not limited to blood, tissue biopsies, spinal fluid, meningeal fluid, urine, alveolar fluid, etc. For those tissue samples in which the cells do not naturally exist in a monolayer, the cells can be dissociated by standard techniques known to those skilled in the art. These techniques include but are not limited to trypsin, collagenase or dispase treatment of the tissue.

In an important specific embodiment, the invention is used to detect and diagnose fetal cells. Our approach is directly opposite to that taken by others seeking a non-invasive method for performing fetal cell based prenatal diagnosis. Rather than attempting substantially to enrich the concentration of fetal cells within a maternal blood sample, our approach involves identifying fetal cells within an unenriched maternal blood sample and subsequently performing diagnostic procedures on the fetal cells so identified, in situ.

Figure 1:
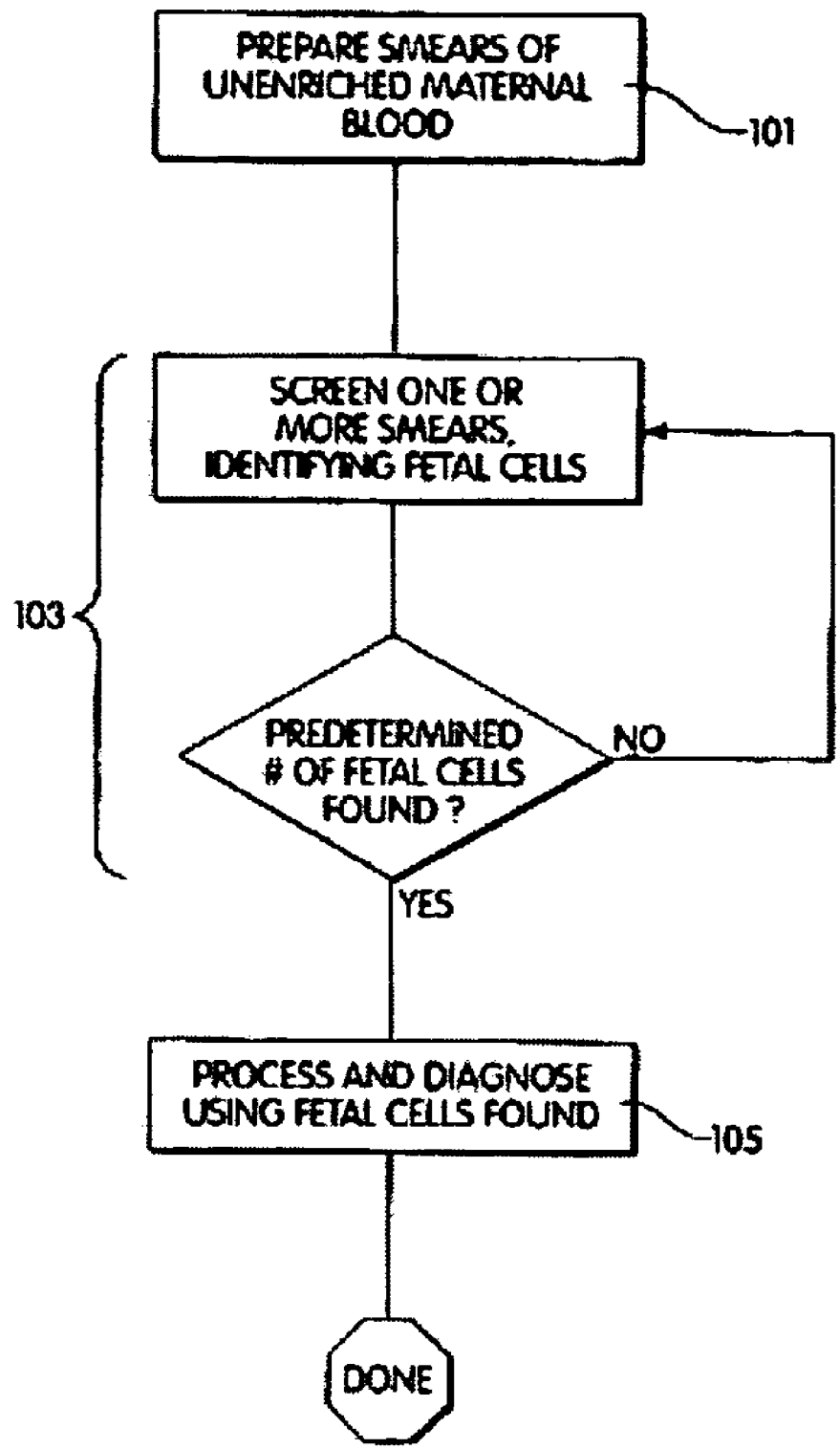
FIG. 1 is a flow chart summarizing the method of one aspect of the invention.

A summary of this new approach, shown in the flow chart of FIG. 1, is as follows:

Prepare one or more blood smears from a sample of unenriched maternal blood 101;

Screen the one or more blood smears until a predetermined number of fetal cells (e.g., nucleated erythrocytes) have been identified and their coordinates defined 103; and Process those smears or coordinates of a smear at which fetal cells have been identified, diagnosing the presence or absence of a particular genetic feature in the fetal cells 105.

In this approach, two signals are defined, referred to hereinafter as the first signal and the second signal. As used herein, "signal" should be taken in its broadest sense, as a physical manifestation which can be detected and identified, thus carrying information. One simple and useful signal is the light emitted by a fluorescent dye selectively bound to a structure of interest. That signal indicates the presence of the structure, which might be difficult to detect absent the fluorescent dye. An alternating signal is the presence (or absence) of detectable structures having predetermined morphological characteristics, such as shape and size.

Screening 103 is based on the first signal. The first signal, which in this exemplary embodiment indicates cell identity, may be generated by a fluorescent dye bound to an antibody against the hemoglobin ε-chain, i.e., embryonal hemoglobin, for example. Alternatively, for example, a metric of each cell's similarity to the characteristic morphology of nucleated erythrocytes, discerned using cell recognition algorithms may serve as the first signal. In yet another example, the first signal may be a measure of the presence of the characteristic color of fetal hemoglobin after staining with eosin and acid hematoxylin. It should now be evident that in embodiments which diagnose fetal conditions any detectable indicator of the presence of fetal cells may serve as the first signal, subject to certain constraints noted below.

Diagnosing 105 can be based on the second signal (or on a combination of a first and second signal). The second signal, which in this exemplary embodiment indicates the presence of a particular genetic characteristic being tested for, may be generated, for example, by in situ PCR-amplification or PCR in situ hybridization or FISH. In another embodiment, the second signal which indicates the presence of a particular genetic characteristic being tested for may be generated using RCA technology as described by Lizardi et al., 1998, Nature Genetics 19: 225-232, entitled "Mutation Detection and Single-Molecule Counting Using Isothermal Rolling-Circle Amplification", the entire disclosure of which is incorporated by reference in its entirety, see, id., FIGS. 1, 4, and 6, incorporated specifically herein by reference; see also, Nilsson et al., 1994, Science 265: 2085-2088; Nilsson et al., 1997, Nature Genet. 16: 252-255; Fire et al., 1995, Proc. Nat'l. Acad. Sci. USA, 92: 4631-4645; and Liu et al., 1996, J. Am. Chem. Soc. 118:1587-1594, each of which is incorporated herein by reference in its entirety. Cells that emit both signals, i.e., the cell is a fetal cell and contains the genetic characteristic being tested for, will be scored. Counts may be maintained of the number and strengths of the first and second signals detected. Of particular interest in some important embodiments is counting occurrences of the second signal in the presence of the first signal. Diagnostic value lies in detecting and counting occurrences of overlap between the two signals, one of which may be rare.

In one embodiment, a specific nucleic acid sequence is detected by FISH. In an exemplary embodiment, FISH comprises hybridizing the denatured test DNA of the rare cell type, e.g. a fetal cell, with a denatured dioxygenin (DIG)-labeled genomic probe. The samples containing the test DNA are washed and allowed to bind to an anti-DIG antibody coupled to a fluorophore. Optionally, a second layer of fluorophore (e.g. FITC) is added by incubation with fluorophore-conjugated anti-Fab antibodies. In a preferred embodiment, FISH comprises hybridizing the denatured DNA of the rare cell with a fluorescently labeled probe comprising DNA sequence(s) homologous to a specific target DNA region (s) directly labeled with a particular fluorophore.

In another preferred embodiment, a specific nucleic acid sequence is detected by RCA. RCA generates multiple copies of a selected region of a target gene as a single stranded DNA. In an exemplary embodiment, detection of the ssDNA produced by RCA comprises in situ probing, with one or multiple probes, partially deproteinized or deproteinized cytological samples suspected of containing a rare cell. The DNA in the cytological sample is denatured prior to RCA. In one mode of the embodiment, detection is achieved by condensation of the ssDNA after hybridization of complementary oligonucleotide tags to the ssDNA (RCA-CACHET format). In yet another embodiment, a hapten such as BUDR is incorporated into the ssDNA. The ssDNA is then contacted with an antibody that recognizes the hapten. The ssDNA-antibody complex can be detected by a label that is conjugated to the antibody, conjugated to a second antibody or, if the antibody is coupled to avidin, by a label that is conjugated to biotin. The detectable label is preferably a fluorophore, but can also be an enzyme that catalyzes a colorimetric reaction such as alkaline phosphatase (AP) or horseradish peroxidase (HRP).

In an illustrative example, a sample of maternal blood suspected of containing fetal cells to be prenatally diagnosed is fixed on a slide and a denatured, partially deproteinized DNA preparation obtained, e.g., by salt-extraction of the cells under alkaline pH. Padlock probe ligation in situ is performed by incubating a reaction mixture under a cover slip, sealed, e.g., with rubber cement, using a mixture comprising a phosphorylated target DNA specific probe, a target DNA gap probe, TRIS buffer, acetylated BSA and DNA ligase, e.g., Ampligase. The slide is washed twice, e.g., in 2×SSC, formamide then Tris Cl buffer, KOAC,MgCl2 and DTT to remove formamide. An RCA reaction is carried out under a coverslip using a reaction buffer, dNTP's and a rolling-circle primer. DNA polymerase, e.g., phageE 20 DNA polymerase, is added and the reaction mixture incubated; the slide is washed and incubated in a labeled antibody, e.g., a biotinylated-BUDR-IgG. After washing, the slide is incubated with a signal producing label, e.g., FITC-avidin, stained, e.g., with 40-6-diamidino-2-phenlidole. For a more detailed description and other illustrative embodiments of RCA signal production and detection, see infra Section 6.1.2.

Automated sample analysis will be performed by an apparatus and method of distinguishing in an optical field objects of interest from other objects and background. An example of an automated system is disclosed in our U.S. Pat. No. 5,352,613, issued Oct. 4, 1994. Furthermore, once an object has been identified, the color, i.e., the combination of the red, green, blue components for the pixels that comprise the object, or other parameters of interest relative to that object can be measured and stored.

Automated sample analysis and diagnosis of a genetic condition could also proceed as follows. The method involves (i) receiving a digitized color image of the fixed sample, which has been subjected to fluorescence in situ hybridization under conditions to specifically hybridize a fluorophor-labeled probe to the target nucleic acid; (ii) processing the color image in a computer to separate objects of interest from background in the color image; (iii) measuring parameters of the objects of interest identifying objects having specific characteristics; (iv) counting the objects identified; and (v) analyzing the count of objects with respect to a statistically expected count to determine the genetic condition. The method is useful for diagnosing genetic conditions associated with an aberration in chromosomal number and/or arrangement. Thus, for example, the invention can be used to detect chromosomal rearrangements by using a combination of labeled probes which detect the rearranged chromosome segment and the chromosome into which the segment is translocated. More generally, as well as trisomy, genetic amplifications and rearrangements including translocations, deletions and insertions can be detected using a method embodying this aspect of the invention in connection with properly selected fluorescent probes.

As used herein, "genetic abnormalities" refers to an aberration in the number and/or arrangement of one or more chromosomes with respect to the corresponding number and/or arrangement of chromosomes obtained from a healthy subject, i.e., an individual having a normal chromosome complement. Genetic abnormalities include, for example, chromosomal additions, deletions, amplifications, translocations and rearrangements that are characterized by nucleotide sequences of, typically, as few as about 15 base pairs and as large as an entire chromosome. Genetic abnormalities also include point mutations.

The method is useful for determining one or more genetic abnormalities in a fixed sample, i.e., a sample attached to a solid support which preferably has been treated in a manner to preserve the structural integrity of the cellular and subcellular components contained therein. Methods for fixing a cell containing sample to a solid support, e.g., a glass slide, are well known to those of ordinary skill in the art.

The sample contains at least one target nucleic acid, the distribution of which is indicative of the genetic abnormality. By "distribution", it is meant the presence, absence, relative amount and/or relative location of the target nucleic acid in one or more nucleic acids (e.g., chromosomes) known to include the target nucleic acid. In a particularly preferred embodiment, the target nucleic acid is indicative of a trisomy 21 and, thus, the method is useful for diagnosing Down's syndrome. In a particularly preferred embodiment, the sample intended for Down's syndrome analysis is derived from maternal peripheral blood. More particularly, cells are isolated from peripheral blood according to standard procedures, the cells are attached to a solid support according to standard procedures (see, e.g., the Examples) to permit detection of the target nucleic acid.

Fluorescence in situ hybridization refers to a nucleic acid hybridization technique which employs a fluorophor-labeled probe to specifically hybridize to and thereby, facilitate visualization of, a target nucleic acid. Such methods are well known to those of ordinary skill in the art and are disclosed, for example, in U.S. Pat. No. 5,225,326; U.S. patent application Ser. No. 07/668,751; PCT WO 94/02646, the entire contents of which are incorporated herein by reference. In general, in situ hybridization is useful for determining the distribution of a nucleic acid in a nucleic acid-containing sample such as is contained in, for example, tissues at the single cell level. Such techniques have been used for karyotyping applications, as well as for detecting the presence, absence and/or arrangement of specific genes contained in a cell. However, for karyotyping, the cells in the sample typically are allowed to proliferate until metaphase (or interphase) to obtain a "metaphase-spread" prior to attaching the cells to a solid support for performance of the in situ hybridization reaction.

Briefly, fluorescence in situ hybridization involves fixing the sample to a solid support and preserving the structural integrity of the components contained therein by contacting the sample with a medium containing at least a precipitating agent and/or a crosslinking agent. Exemplary agents useful for "fixing" the sample are described in the Examples. Alternative fixatives are well known to those of ordinary skill in the art and are described, for example, in the above-noted patents and/or patent publications.

In situ hybridization is performed by denaturing the target nucleic acid so that it is capable of hybridizing to a complementary probe contained in a hybridization solution. The fixed sample may be concurrently or sequentially contacted with the denaturant and the hybridization solution. Thus, in a particularly preferred embodiment, the fixed sample is contacted with a hybridization solution which contains the denaturant and at least one oligonucleotide probe. The probe has a nucleotide sequence at least substantially complementary to the nucleotide sequence of the target nucleic acid. According to standard practice for performing fluorescence in situ hybridization, the hybridization solution optionally contains one or more of a hybrid stabilizing agent, a buffering agent and a selective membrane pore-forming agent. Optimization of the hybridization conditions for achieving hybridization of a particular probe to a particular target nucleic acid is well within the level of the person of ordinary skill in the art.

In reference to a probe, the phrase "substantially complementary" refers to an amount of complementarity that is sufficient to achieve the purposes of the invention, i.e., that is sufficient to permit specific hybridization of the probe to the nucleic acid target while not allowing association of the probe to non-target nucleic acid sequences under the hybridization conditions employed for practicing the invention. Such conditions are known to those of ordinary skill in the art of in situ hybridization.

The genetic abnormalities for which the invention is useful are those for which there is an aberration in the number and/or arrangement of one or more chromosomes with respect chromosomes obtained from an individual having a normal chromosome complement. Exemplary chromosomes that can be detected by the present invention include the human X chromosome, the Y chromosome and chromosomes 13, 18 and 21. For example, the target nucleic acid can be an entire chromosome, e.g., chromosome 21, wherein the presence of three copies of the chromosome ("the distribution" of the target nucleic acid) is indicative of the genetic abnormality, Down's syndrome). Exemplary probes that are useful for specifically hybridizing to the target nucleic acid (e.g. chromosome) are probes which can be located to a chromosome (s) that is diagnostic of a genetic abnormality. See e.g., Harrison's Principles of Internal Medicine, 12th edition, ed. Wilson et al., McGraw Hill, N.Y., N.Y. (1991).

The preferred embodiment of the invention is directed to the prenatal diagnosis of Down's syndrome by detecting trisomy 21 (discussed below) in fetal cells present in, for example, maternal peripheral blood, placental tissue, chorionic villi, amniotic fluid and embryonic tissue. However, the method of the invention is not limited to analysis of fetal cells. Thus, for example, cells containing the target nucleic acid may be eukaryotic cells (e.g., human cells, including cells derived from blood, skin, lung, and including normal as well as tumor sources); prokaryotic cells (e.g., bacteria) and plant cells. According to one embodiment, the invention is used to distinguish various strains of viruses. According to this embodiment, the target nucleic acid may be in a non-enveloped virus or an enveloped virus (having a non-enveloped membrane such as a lipid protein membrane). See, e.g., Asgari supra. Exemplary viruses that can be detected by the present invention include a human immunodeficiency virus, hepatitis virus and herpes virus.

The oligonucleotide probe is labeled with a fluorophor (fluorescent "tag" or "label") according to standard practice. The fluorophor can be directly attached to the probe (i.e., a covalent bond) or indirectly attached thereto (e.g., biotin can be attached to the probe and the fluorophor can be covalently attached to avidin; the biotin-labeled probe and the fluorophor-labeled avidin can form a complex which can function as the fluorophor-labeled probe in the method of the invention).

Fluorophors that can be used in accordance with the method and apparatus of the invention are well known to those of ordinary skill in the art. These include 4,6-diamidino-2phenylindole (DIPA), fluorescein isothiocyanate (FITC) and rhodamine. See, e.g., the Example. See also U.S. Pat. No. 4,373,932, issued Feb. 15, 1983 to Gribnau et al., the contents of which are incorporated herein by reference, for a list of exemplary fluorophors that can be used in accordance with the methods of the invention. The existence of fluorophors having different excitation and emission spectrums from one another permits the simultaneous visualization of more than one target nucleic acid in a single fixed sample. As discussed below, exemplary pairs of fluorophors can be used to simultaneously visualize two different nucleic acid targets in the same fixed sample.

The distribution of the target nucleic acid is indicative of the genetic abnormality. See e.g., Asgari supra. The genetic abnormalities of the invention include mutations, deletions, additions, amplifications, translocations and rearrangements. For example, a deletion can be identified by detecting the absence of the fluorescent signal in the optical field. To detect a deletion of a genetic sequence, a population of probes are prepared that are complementary to a target nucleic acid which is present in a normal cell but absent in an abnormal one. If the probe (s) hybridize to the nucleic acid in the fixed sample, the sequence will be detected and the cell will be designated normal with respect to that sequence. However, if the probes fail to hybridize to the fixed sample, the signal will not be detected and the cell will be designated as abnormal with respect to that sequence. Appropriate controls are included in the in situ hybridization reaction in accordance with standard practice known to those of ordinary skill in the art.

A genetic abnormality associated with an addition of a target nucleic acid can be identified, for example, by detecting binding of a fluorophor-labeled probe to a polynucleotide repeat segment of a chromosome (the target nucleic acid). To detect an addition of a genetic sequence (e.g., trisomy 21), a population of probes are prepared that are complementary to the target nucleic acid. Hybridization of the labeled probe to a fixed cell containing three copies of chromosome 21 will be indicated as discussed in the Examples.

Amplifications, mutations, translocations and rearrangements are identified by selecting a probe which can specifically bind to a break point in the nucleic acid target between a normal sequence and one for which amplification, mutation, translocation or rearrangement is suspected and performing the above-described procedures. In this manner, a fluorescent signal can be attributed to the target nucleic acid which, in turn, can be used to indicate the presence or absence of the genetic abnormality in the sample being tested. The probe can have a sequence that is complementary to the nucleic acid sequence across the break point in a normal individual's DNA, but not in an abnormal individual's DNA. Probes for detecting genetic abnormalities are well known to those of ordinary skill in the art.

Each of the above-identified patents, patent publications and references is incorporated in its entirety herein by reference.

Figure 3:
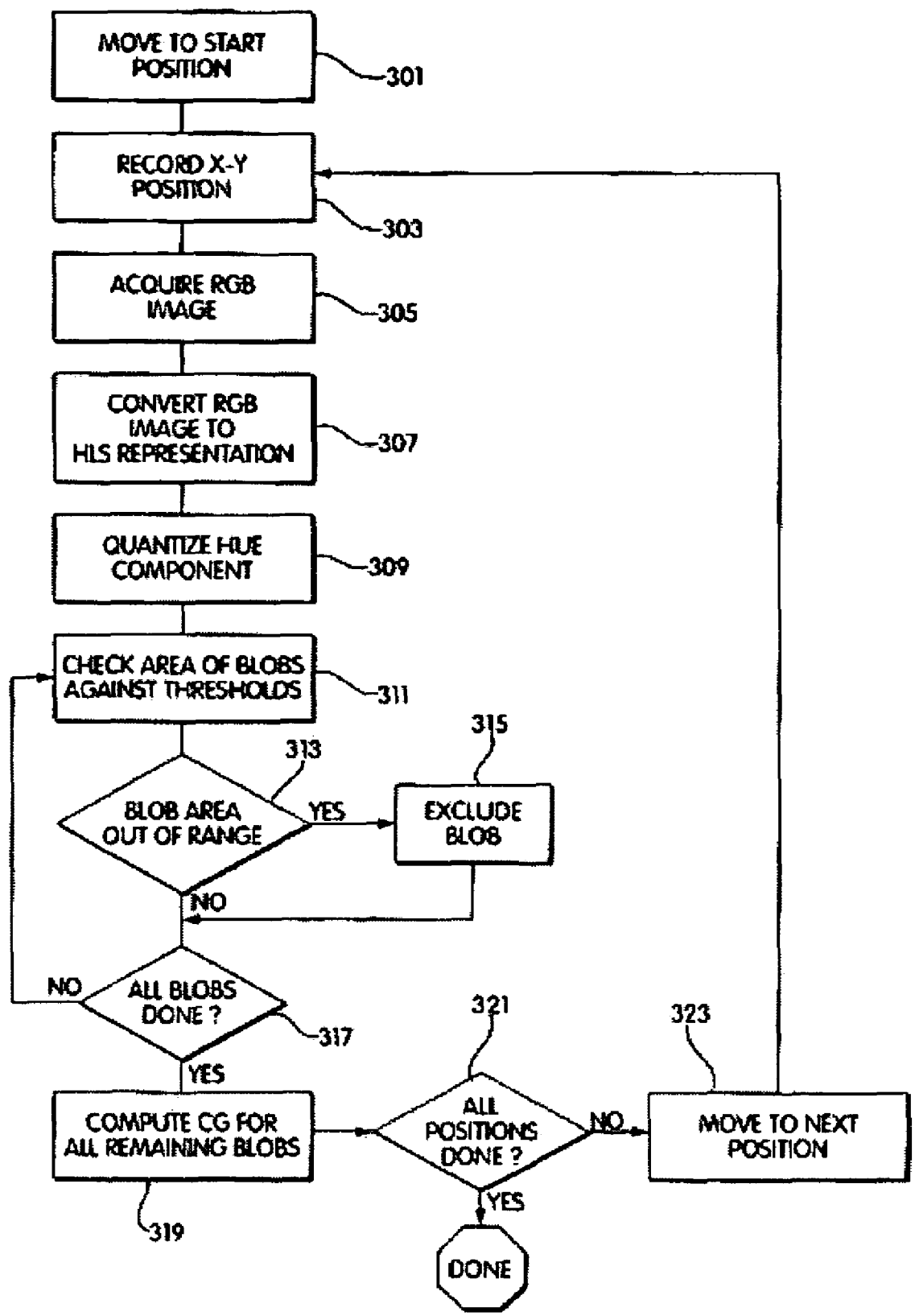
FIG. 3 is a flow chart of stage I leading to detecting the first signal.

Another example of an apparatus and method for automated sample analysis is presented, infra, in Section 6, Exemplary Embodiments, in particular Sections 6.2.1, 6.2.2 and 6.3, and is illustrated in FIGS. 3-5.

In one embodiment of the invention, the system consists of an automatic microscopical sample inspection system having:
  a sample storage and loading and unloading module
  a sample transporting mechanism to and from an automated stage that moves the sample under a microscope objective lenses array
  an array of CCD cameras
  a processing unit having a host computer, multiple controllers to control all mechanical parts of the microscopy system and
  a high speed image processing unit where the CCD cameras are connected.

An innovative feature of this embodiment of a computer controlled system is an array of two or more objective lenses having the same optical characteristics, depicted in FIG. 8.

The lenses are arranged in a row and each of them has its own z-axis movement mechanism, so that they can be individually focused (801). This system can be equipped with a suitable mechanism so that the multiple objective holder can be exchanged to suit the same variety of magnification needs that a common single-lens microscope can cover. Usually the magnification range of light microscope objectives extends from 1× to 100×.

Each objective is connected to its own CCD camera (803). The camera field of view characteristics are such that it acquires the full area of the optical field as provided by the lens.

Each camera is connected to an image acquisition device (804). This is installed in a host computer. For each optical field acquired, the computer is recording its physical location on the microscopical sample. This is achieved through the use of a computer controlled x-y mechanical stage (805). The image provided by the camera is digitized and stored in the host computer memory. With the current system, each objective lens can simultaneously provide an image to the computer, each of which comprises a certain portion of the sample area. The lenses should be appropriately corrected for chromatic aberrations so that the image has stable qualitative characteristics all along its area.

The imaged areas will be in varying physical distance from each other. This distance is a function of the distance at which the lenses are arranged and depends on the physical dimensions of the lenses. It will also depend on the lenses' characteristics, namely numerical aperture and magnification specifications, which affect the area of the optical field that can be acquired. Therefore, for lenses of varying magnification/numerical aperture, the physical location of the acquired image will also vary.

The computer will keep track of the features of the objectives-array in use as well as the position of the motorized stage. The stored characteristics of each image can be used in fitting the image in its correct position in a virtual patchwork, i.e. "composed" image, in the computer memory as shown in FIG. 9.

For example, when starting the host computer moves the sample stage to an initial ($x_1$, $y_1$) position. Following the acquisition of the images at this position, the stage moves to a new ($x_2$, $y_2$) position, in a side-wise manner. Then a new set of images is acquired and also stored. As shown in FIG. 9 at a certain step 1, the image segments denoted "1" are captured and stored. In step 2, the segments "2" are stored. In step 3, the segments "3" restored. The complete image is "composed" in the computer memory as the successive image segments are acquired.

The host computer system that is controlling the above configuration, is driven by software system that controls all mechanical components of the system through suitable device drivers. The software also comprises properly designed image composition algorithms that compose the digitized image in the computer memory and supply the composed image for processing to further algorithms. Through image decomposition, synthesis and image processing specific features particular to the specific sample are detected.

In all automated sample analysis embodiments of the invention, if the generation of the first signal is measured first, indicating cell identity, the one or more smears will be observed using an automated optical microscope to delineate coordinates of a desired number of fetal cells (or other rare cells). Only those smears found to contain fetal cells (or other rare cells) need be treated to generate the second signal, indicating the presence of the particular genetic characteristic being tested for. The automated image analysis algorithms will search for the presence of the second signal at predetermined coordinates of fetal cells (or other rare cells) and also at predetermined coordinates of control maternal cells. This process could be reversed, whereby the genetic abnormality signal is observed first, and then the cell emitting that signal could be observed to determine whether it is a fetal cell. It is even possible to observe both signals simultaneously, searching only for the simultaneous presence of two signals at a single set of coordinates or even a single signal which results from the interaction of two components (e.g. a quenching of a first signal by a partner' signal', the first signal being for the cell type and the partner' signal being for the genetic abnormality).

The requirements and constraints on the generation of the first and second signals are relatively simple. The materials and techniques used to generate the first signal should not interfere adversely with the materials and techniques used to generate the second signal (to an extent which compromises unacceptably the diagnosis), and visa versa. Nor should they damage or alter the cell characteristics sought to be measured to an extent that compromises unacceptably the diagnosis. Finally, any other desirable or required treatment of the cells should also not interfere with the materials or techniques used to generate the first and second signals to an extent that compromises unacceptably the diagnosis. Within those limits, any suitable generators of the first and second signals may be used.

This exemplary embodiment of the invention may be characterized thus: (i) rather than attempting to enrich (or to further enrich if already partially enriched) the concentration of fetal cells within the maternal blood, fetal cells within the unenriched maternal blood sample are identified for further processing; and (ii) a suitable single cell detection method, such as in situ PCR and/or PCR in situ hybridization is performed to determine the presence of a genetic characteristic being tested for, in some instances only on smears or coordinates of smears that have already been stained and processed, and within which fetal cells have been detected.

Although in an important embodiment, the maternal blood used contains a naturally present concentration of fetal cells, the invention is meant to embrace also maternal blood which has been partially or even substantially enriched for fetal cells. According to the prior art, the goal was to obtain as much enrichment as possible, to achieve concentrations of fetal cells greater than one fetal cell per 1000 maternal cells. It in particular was the goal to completely isolate fetal cells from maternal cells. According to the invention, cell samples are used where the rare cell is present at no greater than one in every 10,000 cells (i.e., no greater than 0.01%). Thus, simple procedures may be employed to partially enrich the maternal blood sample for fetal cells, such as using simple fractionation procedures (e.g. centrifugation or density gradients) and the like. The procedure falls within the scope of the invention when the sample of cells containing the rare cell is used where the rare cell is present at no greater a concentration than 0.01%. As mentioned above, the invention also in very important embodiments is used where the concentration of the rare cell is 0.001%, 0.0001%, 0.00001%, 0.000001%, and even 0.0000001%. The typical concentration of fetal cells in maternal blood is between one fetal cell in 10⁵ maternal cells to one fetal cell in 10⁹ maternal cells. Thus, the invention is useful over the full-range of concentrations of fetal cells in maternal blood as typically occurs naturally.

In one specific embodiment of the invention, when the rare cell type is present in the sample, the method of the invention detects the rare cell type at a frequency of no less than 80%. In other embodiments, the detection frequencies are no less than 85%, 90%, 95% and 99%.

In addition to the detection of genetic abnormalities in a developing fetus, the above-described method is applicable to any situation where rare event detection is necessary. In particular, the invention can be applied in any situation where a signal from a rare cell is to be detected where the rare cell is present at a concentration no greater than one rare cell for every 10,000 other cells. The invention is particularly applicable to those circumstances where the rare cell can be distinguished phenotypically or otherwise from the other cells whereby the rare cell first is identified using a first signal, and then the genetic characteristics of the cell identified are determined using a second signal. For example, the signal identifying the rare cell may be produced by a probe specific to the type of rare cell. Alternatively, the signal identifying the rare cell may be computed from measurements of morphological characteristics of the cell. Indeed, the rare event need not be the occurrence of a particular cell type, at all, but could instead by defined by the presence of a particular intracellular structure or molecule which is detectable by similar signal generation and detection methods.

Virtually any chromosomal abnormality or Mendelian trait could be diagnosed using the present technology. The only prerequisite is knowledge of the underlying molecular defect. Use of single fluorophores for the tagging of an individual allele creates an upper limit as to the number of mutations that can be tested simultaneously, however use of combinatorial chemistry increases enormously the number of allele specific mutations that can be tagged and detected simultaneously. Chromosomal abnormalities that fall within the scope of the invention include but are not limited to Trisomy 21, 18, 13 and sex chromosome aberrations such as XXX, XXY, XYY. With the use of combinatorial chemistry, the methods of the invention can be used to diagnose a multitude of rearrangements, including translocations observed in genetic disorders and cancer. Mendelian disorders that fall within the scope of the invention include but are not limited to cystic fibrosis, hemochromatosis, hyperlipidemias, Marfan syndrome and other heritable disorders of connective tissue, hemoglobinopathies, Tay-Sachs syndrome or any other genetic disorder for which the mutation is known. The use of combinatorial chemistry dyes allows for the simultaneous tagging and detection of multiple alleles thus making it possible to establish the inheritance of predisposition of common disorders, e.g. asthma and/or the presence of several molecular markers specific for cancers, e.g., prostate, breast, colon, lung, leukemias, lymphomas, etc.

One particularly important use of the invention is in the field of cancer. Cancer cells of particular types often can be recognized morphologically against the background of non-cancer cells. The morphology of cancer cells therefore can be used as the first signal. Heat shock proteins also are markers expressed in most malignant cancers. Labeled antibodies, such as fluorescently-tagged antibodies, specific for heat shock proteins can be used to generate the first signal. Likewise, there are antigens that are specific for particular cancers or for particular tissues, such as Prostate Specific Antigen, and antibodies specific for cancer or tissue antigens, such as Prostate Specific Antigen can be used to generate a first signal for such cancer cells.

Once a cancer cell has been identified by the first signal, a second signal can be generated for providing more information about the cancer. For example, the lifetime risk of breast cancer approaches 80-90% in women with a germ line mutation in either BRCA 1 or BRCA2. A variety of mutations in these genes are known and have been reported.

Prostate cancer is somewhat unique in its presentation to the pathologist of a bewildering array of histologies difficult to assign to diagnostic criteria. It is important to analyze and record the genetic alterations found in prostate cancer, with the objective of correlation to the pathology and natural history of the disease. Such genetic alterations include known alterations in P53, ras, Rb, cyclin-dependent kinases, oncogenes and tumor suppressors. T-cell receptor gene rearrangements are known in large granular lymphocyte proliferations. T-cell receptor delta gene rearrangements are known in acute lymphoblastic leukemia and non-Hodgkin's lymphoma.

Thus, rare cancer cells in a background of other cells can be identified and characterized according to the invention. The characterization may include a confirmation of a diagnosis of the presence of the cancer cell, a determination of the type of cancer, a determination of cancer risk by determining the presence of a marker of a genetic change which relates to cancer risk, etc. Some of the following markers can be used either as the first or the second signals depending on the purpose to which the invention is directed, as will be recognized by those of ordinary skill in the art. The markers include:

Human tumor specific antibody GM4. It preferentially reacts with melanomas and neuroblastomas.

Bone morphogenic proteins (BMPs). Bone metastasis is a common event in prostate cancer and some of the BMPs are expressed in prostate cancer cells.

Growth regulatory genes. Alterations in the structure and expression of growth regulatory genes can lead to the initiation of malignant transformation and tumor progression.

Protein tyrosine kinases. Such kinases are over-expressed in esophageal cancer and play an important role in regulation of proliferation.

Telomerase (hTRT). Elevated expression of hTRT occurs in some cancer tissues.

p53, c-erbB-2 and p21ras. These genes are over expressed in ovarian neoplasms.

Development of ovarian carcinoma is the end result of action of several cancer causing genes.

BCL-2 family of proto-oncogenes. These genes are critical regulators of apoptosis whose expression frequently becomes altered in human cancers (including some of the most common types of leukemias and lymphomas).

eKi-ras and c-myc. Mutation of these genes is implicated in tumor initiation and progression in rectal cancer.

APC, p53 and DCC. These are implicated in colorectal tumor carcinogenesis.

Treatment strategies need to be co-ordinated with knowledge of the behavior of the tumor based on its genetic fingerprint.

Markers of genetic changes enable assessment of cancer risk. They provide information on exposure to carcinogenic agents. They can detect early changes caused by exposure to carcinogens and identify individuals with a particularly high risk of cancer development. Such markers include LOH on chromosome 9 in bladder cancer, and chromosomelp deletions and chromosome 7, 17 and 8 gains/losses detected in colorectal tumorigenesis.

Development of lung cancer requires multiple genetic changes. Activation of oncogenes includes K-ras and myc. Inactivation of tumor suppressor genes includes Rb, p53 and CDKN2. Identification of specific genes undergoing alteration is useful for the early detection of cells destined to become malignant and permits identification of potential targets for drugs and gene-based therapy.

Another type of cancer which involves multiple genetic changes is adenometous polyposis colon (APC), commonly referred to as colon cancer. Development of APC is characterized by a cascade of mutations affecting up to five genes. Depending on the diagnostic question asked, the doctor may wish to test for from one of five genetic rearrangements or mutations. In this case, the rare event to be indicated by the first signal is the presence of an intestinal epithelial cell. The second signal should indicate one or more of the genetic changes which mark the progression of APC. Counts or ratios among the second signals detected have diagnostic significance which varies depending on where the intestinal epithelial cells were found. Mutated cells found in a peripheral blood sample may be assigned a higher risk of further disease progression than similar cells found in a swab sample of the colon.

Mutations in genes that lie in the retinoblastoma pathway are implicated in the pathogenesis of many tumor types. Two critical components involved in tumor progression are p16/CDKN2A and CDK4. Alterations in the former is well documented in multiple cancers including melanoma. Alterations in the latter are rarer.

Mutations in one of four mismatch repair genes (hMSH2, hMLH1, hPMS1 and hPMS2) account for 70% of HNPCC.

Chromosome 1 1p15. 5 is an important tumor suppressor gene region showing LOH in Wilms tumor, rhabdomyosarcoma, adrenocortical carcinoma and lung, ovarian and breast cancer.

Identification of numerically infrequent leukemic cells via unique genomic fusion sequences include MLL-AF4 and PML/RAR (in acute promyelocytic leukemia).

T-cell receptor gene rearrangements are known in large granular lymphocyte proliferations.

T-cell receptor delta gene rearrangements are known in acute lymphoblastic leukemias and non-Hodgkin's lymphoma.

FAP is caused by mutations in the APC gene resulting in multiple adenomas of the colorectal mucosa.

We have found that a count of events marked by the second signal, a ratio between counts of events marked by different second signals, and a ratio between a count of events marked by the second signal and a count of the rare event marked by the first signal has diagnostic significance in numerous clinical settings. Specific numeric counts are therefore obtained in embodiments of the invention, rather than or in addition to measures of signal strength, if desired.

For example, consider Mendelian disorders which result from the presence of a normal and mutated allele. Probes for both the normal allele and the mutated allele are used to generate two distinct second signals. The ratio of counts has diagnostic significance in that 100% normal alleles can indicate a normal individual, 50% normal and 50% mutated alleles can indicate a carrier individual, and 100% mutated alleles can indicate an affected individual. In order to detect the ratio, both probes are used and corresponding signal occurrences counted.

Consider, also, conditions which are mosaic, in which the degree to which an individual is affected by a genetic anomoly depends upon a ratio of the number of cells affected by the anomoly to the number of cells not affected. For example, Down's syndrome is occasionally mosaic. By counting trisomy 21 signals and comparing the count to diploid chromosome 21 signals, the degree to which an individual is affected can be determined. In order to obtain a useful ratio, the rare cells, i.e., fetal cells, are first identified using a suitable first signal as explained above.

Translocation defects in a chromosome were conventionally detected by using probes directed to two adjacent or nearby portions of the chromosome. When the probes are separated, a translocation has occurred. However, such an event would be difficult to detect automatically. Instead, according to some embodiments of the invention, a probe which hybridizes with the anticipated break region is used. Then, the count of signals from this probe is indicative of the presence or absence of the probed-for translocation.

Thus, it can be seen according to an important aspect of the invention that numerical information about the signals is obtained and compared to other numerical information of another signal or to diagnostically relevant information such as tissue type or statistical information about a disorder to generate diagnostic information. The following additional examples may be instructive.

In determining risk of cancer, the number of signals in one tissue type may be indicative of a particular risk whereas the same number of signals in a different tissue type may yield a different risk. The tissue type may be known in advance, or may be determined using the imaging techniques of the invention. In addition, the number of different signals (for example indicating mutations) in a single cell may be important to evaluating risk. Thus, the computer image implemented procedure may determine the number of different signals in a single cell and maybe even the cell type. The ratio of one signal to another may be important or even the ratio of one signal in one cell type to the same or different signal in another cell type. These parameters are well known to those skilled in this art.

In determining trisomy, the invention contemplates determining the presence of trisomy in a single cell, and/or determining the frequency of single cells with trisomy in a population of cells (which could be done without knowing which cells are trisomic; i.e. total number of cells counted and total number of chromosomes counted). The existence of trisomy or the risk of a condition associated with trisomy then could be evaluated.

Important is the recognition that signals can be counted and be compared to other information (e.g. other signal counts, statistical information about predicted signal frequency for different tissue types, etc.) so as to yield relevant diagnostic information.

The invention is described in connection with observing "monolayers" of cells. Monolayer has a specific meaning as used herein. It does not require confluence and can involve single cell suspensions. It means simply that the cells are arranged whereby they are not stacked on top of one another, although all of the cells can be separated from one another. Thus, monolayers can be smears of single cell suspensions or can be a thin layer of tissue. Any solid or exfoliative cytology technique can be employed.

The invention also has been described in connection with identifying a pair of signals, one which identifies a target rare cell such as a fetal cell and another which is useful in evaluating the state of the cell such as a fetal cell having a genetic defect. It should be understood that according to certain embodiments, only a single signal need be detected. For example, where a fetal cell carries a Y chromosome and the diagnosis is for an abnormality on the Y chromosome, then the signal which identifies the genetic abnormality can be the same as that which identifies the fetal cell. As another example, a single signal can be employed in circumstances where the observed trait is a recessive trait. A pair of signals also can be used to detect the presence of two alleles or the existence of a condition which is diagnosed by the presence of two or more mutations in different genes. In these circumstances the pair of signals (or even several signals) can identify both the phenotype and the cell having that phenotype. Such embodiments will be apparent to those of ordinary skill in the art.

6. EXEMPLARY EMBODIMENTS 6.1. Smear Preparation

Smears were prepared from 10 pl aliquots of whole blood on glass microscope slides. Smears were prepared from both cord blood and maternal circulating blood and allowed to air dry.

6.1.1. Cell Fixation

Fixation of smears prior to cell permeabilization for in situ PCR or PCR in situ hybridization was under one of three conditions. (i) Smears were fixed in ice-cold methanol for 10 minutes-16 hours. (ii) Smears were fixed in ice-cold 10% buffered formalin for 10 minutes-16 hours. (iii) Smears were fixed in 2% paraformaldehyde for 10 minutes-16 hours. Following fixation, smears were washed three times in phosphate buffered saline, at room temperature, for 10 minutes. Smears were then air-dried.

6.1.2. Cell Staining

Polychrome staining: The smears were covered with Wright's stain and incubated for one to two minutes at room temperature. Distilled water (2.5 ml) was then added to dilute the stain and incubation at room temperature continued for 3-6 minutes. The stain was then washed off rapidly with running water and a 1:10 dilution of Giemsa stain added to the slide. Incubation was at room temperature for 5 minutes and the stain was then washed off rapidly with running water. The smears were then air-dried.

Antibody staining: The smears were covered with anti-embryonal hemoglobin (hemoglobins-chain) monoclonal antibody and incubated at room temperature for one to three hours. The slides were then washed twice in phosphate buffered saline, at room temperature, for 5 minutes. Secondary antibody (anti-mouse antibody conjugated to phycoerythrin) was then added and the slide incubated at 37 C for 30 minutes. The slides were then washed twice in phosphate buffered saline, at room temperature, for 5 minutes and air-dried.

Fetal hemoglobin staining: Smears were fixed in 80% ethanol for 5 to 10 minutes, then rinsed with tap water and air dried. Acid citrate-phosphate buffer (37.7 ml 0.1M citric acid, 12.3 ml 0.2MNa2HP04, pH3.3) was pre-warmed in a coplin jar in a 37° C. water bath. The fixed smears were then added to the coplin jar and incubated at 37° C. for 5 minutes. The smears were then rinsed with tap water and stained with 0.1% hematoxylin for one minute. The smears were then rinsed with tap water and stained with 0.1% eosin for one minute. The smears then underwent a final rinse in tap water and were air-dried.

Cell Permeabilization: Cell permeabilization was attained by incubation in either proteinase K (1-5 mg/ml in phosphate buffered saline) or pepsin (2-5 mg/ml in 0.01M hydrochloric acid). Incubation was at room temperature for 1-30 minutes. Following permeabilization, smears were washed in phosphate buffered saline, at room temperature, for 5 minutes, then in 100% ethanol, at room temperature, for one minute. Smears were then air dried.

PCR In Situ Hybridization: For PCR in situ hybridization, smears were overlaid with 50 pl amplification solution. Amplification solution comprised 1 OmM TriHCI, pH8.3, 90 mM potassium chloride, 1-5 mM magnesium chloride, 200 uM dATP, 200 uM dCTP, 200 uM dGTP, 200 pM dTTP, 1 pM forward primer, 1 uM reverse primer and 5-10 units thermostable DNA polymerase in aqueous sealing reagent. A glass coverslip was then lowered onto the amplification solution and the slide transferred to a thermal cycler. Following an initial denaturation step at 94 C for 4 minutes, the slide was then subjected to 25-35 cycles of amplification, where each cycle consisted of denaturation at 94 C for one minute, annealing at 55 C for one minute and extension at 72 C for one minute. The coverslip was then removed by incubation of the slide in phosphate buffered saline for 10 minutes at room temperature, and the slide air-dried. Fluorescein labeled oligonucleotide probe in hybridization buffer (600 mM sodium chloride, 60 mM sodium citrate, 5% dextran sulfate, 50% formamide) was then added and the slide covered with a glass cover slip, and incubated at 94 C for 10 minutes then at 37 C for one hour. The coverslip was then removed by incubation of the slide in phosphate buffered saline for 10 minutes at room temperature and the slide then washed twice for 5 minutes in phosphate buffered saline at room temperature. The smear was then covered with protein block solution (1% bovine serum, 2.5% goat serum, 0.2% Tween-20) and incubated at room temperature for 10 minutes. The solution was then removed and the slide washed three times in phosphate buffered saline for 5 minutes at room temperature. The smear was then covered with mouse anti-fluorescein monoclonal antibody and incubated at room temperature for 20 minutes. The solution was then removed and the slide washed three times in phosphate buffered saline for 5 minutes at room temperature. The smear was then covered with biotinylated goat anti-mouse F (ab)2 and incubated at room temperature for 20 minutes. The solution was then removed and the slide washed three times in phosphate buffered saline for 5 minutes at room temperature. The smear was then covered with alkaline phosphatase conjugated streptavidin and incubated at room temperature for 20 minutes. The solution was then removed and the slide washed twice in phosphate buffered saline for 5 minutes at room temperature. Alkaline phosphatase substrate solution (50 mg/ml BCIP, 75 mg/ml NBT) was then added to the smear and the slide incubated at 37 C for 10 minutes-two hours. The slide was then washed twice in distilled water at room temperature for 5 minutes and air-dried.

In Situ PCR: For in situ PCR, smears were overlaid with 50 Pl amplification solution. Amplification solution comprised 10 mM Tris-HCl, pH8.3.90 mM potassium chloride, 1-5 mM magnesium chloride, 200 µM dATP, 200 µM dCTP, 200 µM dGTP, 0.5 pM [R 110] dUTP, 1 uM forward primer, 1 uM reverse primer and 5-10 units thermostable DNA polymerase in aqueous sealing reagent. A glass coverslip was then lowered onto the amplification solution and the slide transferred to a thermal cycler. Following an initial denaturation step at 94 C for 4 minutes, the slide was then subjected to 25-35 cycles of amplification, where each cycle consisted of denaturation at 94 C for one minute, annealing at 55 C for one minute and extension at 72° C. for one minute. The coverslip was then removed by incubation of the slide in phosphate buffered saline for 10 minutes at room temperature and the slide air-dried.

Rolling Circle Amplification (RCA): Generation and detection of the second signal by a RCA is done according to the methods of Lizardi et al. (1998, Nat. Genet. 19: 225-232). 10 of maternal blood is smeared on a lysine-coated slide and allowed to dry. The smear is fixed in 80% methanol for 5-10 minutes. The DNA in the smear is deproteinized then denatured then rinsed with water and air dried. Alternatively, the maternal blood suspected of containing fetal cells can be prepared using a halo prep (Vogelstein et al., 1980, Cell 22: 79-85; Gerdes et al., 1994, J. Cell Biol. 126: 289-304 each incorporated herein by reference in their entirety).

A target mutant allele is amplified by RCA method, which generates a linear single stranded DNA (ssDNA) molecule comprising tandem repeats of a circular probe, then the ssDNA molecule is detected. In the amplification step, the slide is incubated at 31° C. for 15 minutes in the presence of 50 01 of a solution containing: a circular "padlock" DNA probe of 90 bases comprising 25 bases of target allele-specific sequences generated in situ as described below, 600 nM rolling-circle primer (an oligonucleotide primer of 20 bases that binds to the circular DNA probe adjacent to the target binding site) in 50 mM TrisDHCI (pH 7.5), 10 mM MgCl2, 200 Dg/ml acetylated BSA (Amersham), 400 µM dATP, dGTP, dCTP and dTTP, 40 ng/01 phage T4 gene-32 protein, and 6.3 ng/01 phage029 DNA polymerase. Optionally, BUDR is added to the amplification mixture for incorporation into ssDNA.

The circular oligonucleotides used in the amplification step are generated in situ using gap oligonucleotides and target allele-specific gap-filling oligonucleotides. The gap and gap-filling nucleotides are ligated in situ to generate a closed circular oligonucleotide as a template for amplification. The gap oligonucleotide comprises two 20 nucleotide stretches corresponding to the target gene at each end, wherein the adjacent stretches are 6 nucleotides apart in the target gene. Between the sequences corresponding to the target gene there are 50 random nucleotides, for a total of 90 bases. The gap-filling oligonucleotides are allele-specific and correspond to the 6-nucleotide stretch of the target gene lacking from the gap oligonucleotide. For a combined gap-filling and ligation reaction, the slide is incubated at 62 for 2 hours in the presence of 150 nM phosphorylated open circle gap oligonucleotide, 1200 nM of mutant gap-filling oligonucleotide, 20 mM TrisDHCI (pH 8.3), 50 mMKCI, 10 mMMgCl2, 0.5 mM NAD, 150 Dg/ml acetylated BSA, 0.01% Triton-X-100 and 0.7 U/Ol Ampligase DNA ligase. The slide is then washed twice for 5 minutes at 500 CC in 2×SSC, 25% formamide, then washed for 2 minutes in 50 mM Tris-Cl, pH 7.5, 40 mM KOAC, 10 mM MgCl2, 10 mM DTT, 100 Og/ml BSA to remove formamide prior to amplification.

All enzymatic reactions are carried out by sealing the reaction mixture on the slide with a cover slip sealed with rubber cement. The slide is then placed on a heating block in a humidified chamber.

The amplified ssDNA, if present, can be detected by one of two ways. In the first method, in which BUDR is incorporated with the ssDNA, slides are washed twice for 5 minutes in 2×SSC with 20% formamide at 25 duc following the amplification step, then washed twice for 4 minutes in SSC-BSAT (2×SSC, 2.8% BSA, 0.2% Tween-20) at 370 C. The slides are then incubated for 20 minutes at 37 duc SSC-BSAT containing 5 µg/ml biotinylated anti-BUDR IgG. The slides are then washed three times for 5 minutes in SSC-BSAT containing 5 Og/ml FITC-avidin. After three washes in SSC-BSAT, the slides are stained for 2 minutes in 2×SSC, 0.1 Og/ml 4'6-diamidino-2-phenlindole, washed for 10 minutes in a solution of 1.5×SSC, 0.01% TWEEN-20 at room temperature and prepared for imaging by covering with 20 O1 of Pro-long antifade (Molecular Probes, Inc.) under a cover slip. The slide is returned to the microscope at the coordinates of the fetal cells, and then viewed to determine the absence or presence of signal corresponding to the mutant allele of the target gene.

In the second method of detection, the slides are washed twice for 5 minutes in 2×SSC with 20% formamide at 25 duc following the amplification step, then washed twice for 4 minutes in SSC-BSAT (2×SSC, 2.8% BSA, 0.2% Tween-20) at 370 C. Slides are then incubated in the presence of 0.5 DM of a detection tag oligonucleotide (which is complementary to the ss DNA generated by the amplification reaction and coupled to a fluorophore such as FITC or Cy3) in 2×SSC, 0.05% Triton-X-100, and 0.5 mg/ml degraded herring sperm DNA) for 20 minutes at 37 duc. The slides are washed 4 times for 5 minutes with 2×SSC and 0.1% Triton-X-100, and 4 times for 5 minutes with 4×SSC and 0.1% Triton-X-100, then rinsed once with 2×SSC and drained. The slides are then incubated for 20 minutes at 370 C in condensation solution (330M mouse anti-DNP IgM in 2×SSC, 0.1% Tween-20, 0; 5% BSA, 1 mg/ml degraded herring sperm DNA) then washed twice for 5 minutes in 2×SSC, 0.1% Tween-20 at room temperature, drained and covered with antifade. The slide is returned to the microscope at the coordinates of the fetal cells and viewed to determine the absence or presence of signal corresponding to the mutant allele of the target gene.

A person with skill in the art can recognize the multiple variations on this method that are useful for cell staining and signal generation according to the methods of the present invention. For example, a wild type probe can be used and the presence of a mutant allele detected by the absence of signal. If it is desired to distinguish between two or more alleles of a target gene rather than the presence of a specific mutant allele, the second method of detection is used wherein multiple allele-specific detection tag oligonucleotides are used, each of which is coupled to a different fluorophore. The presence or absence of a given allele is determined by the nature of the fluorophore rather than by the presence or absence of a signal.

6.2. Automated Smear Analysis

Automated smear analysis has been briefly summarized, above. The apparatus and method used in the exemplary embodiment is now described.

6.2.1. Apparatus

Figure 2:
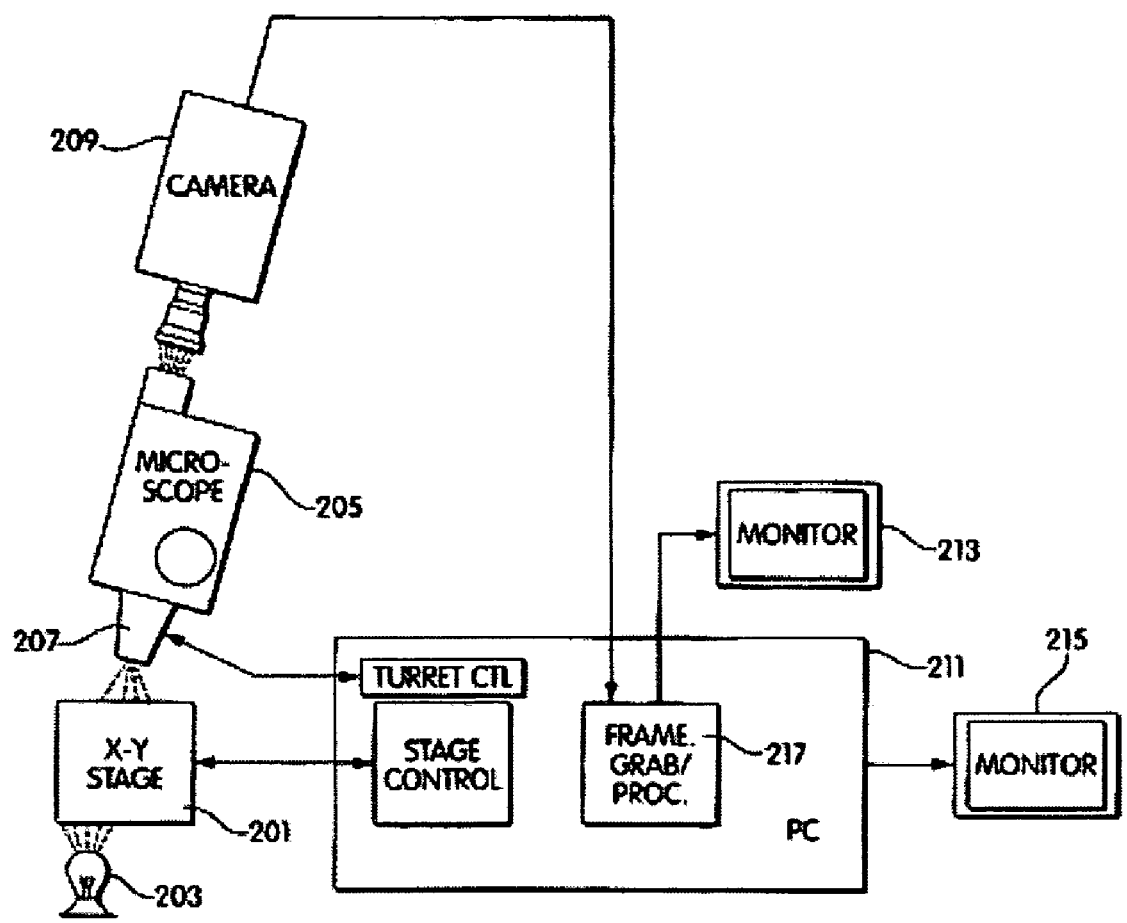
FIG. 2 is a block diagram of an analysis system used in one embodiment of one aspect of the invention.

The block diagram of FIG. 2 shows the basic elements of a system suitable for embodying this aspect of the invention. The basic elements of the system include an X-Y stage 201, a mercury light source 203, a fluorescence microscope 205 equipped with a motorized objective lens turret (nosepiece) 207, a color CCD camera 209, a personal computer (PC) system 211, and one or two monitors 213,215.

The individual elements of the system can be custom built or purchased off the-shelf as standard components. Each element will now be described in somewhat greater detail.

The X-Y stage 201 can be any motorized positional stage suitable for use with the selected microscope 205. Preferably, the X-Y stage 201 can be a motorized stage that can be connected to a personal computer and electronically controlled using specifically compiled software commands. When using such an electronically controlled X-Y stage 201, a stage controller circuit card plugged into an expansion bus of the PC 211 connects the stage 201 to the PC 211. The stage 201 should also be capable of being driven manually. Electronically controlled stages such as described here are produced by microscope manufacturers, for example including Olympus (Tokyo, Japan), as well as other manufacturers, such as LUDL (NY, USA).

The microscope 205 can be any fluorescence microscope equipped with a reflected light fluorescence illuminator 203 and a motorized objective lens turret 207 with a 20× and an oil immersion 60× or 63× objective lens, providing a maximum magnification of 600×. The motorized nosepiece 207 is preferably connected to the PC 211 and electronically switched between successive magnifications using specifically compiled software commands. When using such an electronically controlled motorized nosepiece 207, a nosepiece controller circuit card plugged into an expansion bus of the PC 211 connects the stage 201 to the PC 211. The microscope 205 and stage 201 are set up to include a mercury light source 203, capable of providing consistent and substantially even illumination of the complete optical field.

The microscope 205 produces an image viewed by the camera 209. The camera 209 can be any color 3-chip CCD camera or other camera connected to provide an electronic output and providing high sensitivity and resolution. The output of the camera 209 is fed to a frame grabber and image processor circuit board installed in the PC 211. A camera found to be suitable is the SONY 930 (SONY, Japan).

Various frame grabber systems can be used in connection with the present invention. The frame grabber can be, for example a combination of the MATROX IM-CLD (color image capture module) and the MATROX IM-640 (image processing module) set of boards, available from MATROX (Montreal, CANADA). The MATROX IM-640 module features on-board hardware supported image processing capabilities. These capabilities compliment the capabilities of the MATROX IMAGINGLIBRARY (MIL) software package. Thus, it provides extremely fast execution of the MIL based software algorithms. The MATROX boards support display to a dedicated SVGA monitor. The dedicated monitor is provided in addition to the monitor usually used with the PC system 211. Any monitor SVGA monitor suitable for use with the MATROX image processing boards can be used. One dedicated monitor usable in connection with the invention is a ViewSonic 4E (Walnut Creek, Calif.) SVGA monitor. In order to have sufficient processing and storage capabilities available, the PC 211 can be any INTEL PENTIUM-based PC having at least 32 MB RAM and at least 2 GB of hard disk drive storage space. The PC 211 preferably further includes a monitor. Other than the specific features described herein, the PC 211 is conventional, and can include keyboard, printer or other desired peripheral devices not shown.

6.2.2. Method

The PC 211 executes a smear analysis software program compiled in MICROSOFT C++ using the MATROX IMAGING LIBRARY (MIL). MIL is a software library of functions, including those which control the operation of the frame grabber 211 and which process images captured by the frame grabber 211 for subsequent storage in PC 211 as disk files. MIL comprises a number of specialized image processing routines particularly suitable for performing such image processing tasks as filtering, object selection and various measurement functions. The smear analysis software program runs as a WINDOWS 95 application. The program prompts and measurement results are shown on the computer monitor 213, while the images acquired through the imaging hardware 211 are displayed on the dedicated imaging monitor 215.

In order to process microscopic images using the smear analysis program, the system is first calibrated. Calibration compensates for day to day variation in performance as well as variations from one microscope, camera, etc., to another. During this phase a calibration image is viewed and the following calibration parameters are set:

the color response of the system;

the dimensions or bounds of the area on a on a slide containing a smear to be scanned for fetal cells;

the actual dimensions of the optical field when using magnifications 20× and 60× (or 63×); and the minimum and maximum fetal nuclear area when using magnifications 20× and 60× (or 63×).

6.2.3. Detection of the First (Identification) Signal

The fetal cell detection algorithm operates in two stages. The first is a prescan stage I, illustrated in the flow chart of FIG. 3, where possible fetal cell positions are identified using a low magnification and high speed. The 20× objective is selected and the search of fetal cells can start:

The program moves the automated stage (FIG. 2,201) to a preset starting point, for example one of the corners of a slide containing a smear (Step 301).

The x-y position of the stage at the preset starting point is recorded (Step 303) optical field.

The optical field is acquired (Step 305) using the CCD camera 209 and transferred to the PC 211 as an RGB (Red/Green/Blue) image.

The RGB image is transformed (Step 307) to the ILLS (Hue/Luminance/Saturation) representation.

The Hue component is binary quantized (Step 309) as a black and white image so that pixels with Hue values ranging between 190 and 255 are set to 0 (black) representing interesting areas (blobs), while every other pixel value is set to 255 (white, background). The blobs represent possible fetal cell nuclear areas.

The area of each blob in the binary quantized image is measured. If, at 20× magnification, it is outside a range of about 20 to 200 pixels in size, the blob's pixels are set to value 255 (background); they are excluded from further processing (Steps 311, 313, 315 and 317).

Then the coordinates of each blob's center of gravity (CG) are calculated (Step 319), using a custom MATROX function. The center of gravity of a blob is that point at which a cut-out from a thin, uniform density sheet of material of the blob shape would balance. These coordinates are stored in a database along with the z-y position of the current optical field, so the blob can be located again at the next processing stage using higher magnification.

Additional optical fields are processed similarly, recording the x-y position of each succeeding optical field, until the complete slide are is covered (Steps 321 and 323).

Stage II, illustrated in the flow chart of FIGS. 4A and 4B, includes the final fetal cell recognition process:

63× magnification is selected (Step 401).

The program moves the automated stage (FIG. 2,201) so that the coordinates of the first position of a CG found earlier, which is possible fetal cell nuclear area, is at the center of the optical field (Step 403).

The optical field is acquired using the CCD camera (FIG. 2,209) and transferred to the computer as an RGB image (Step 405).

The RGB image is transformed to the HLS model (Step 407).

The program then generates a Luminance histogram (Step 409) by counting the number of pixels whose Luminance value equals each possible value of Luminance. The counts are stored as an array of length 256 containing the count of pixels having a grey-level value corresponding to each index into the array.

The program next analyzes the Luminance distribution curve (Step 411), as represented by the values stored in the array, and locates the last peak. It has been found that this peak includes pixel values that represent plasma area in the image. The function that analyzes the Luminance distribution curve: calculates a 9-point moving average to smooth the curve; calculates the tangents of lines defined by points 10 grey-level values distant; calculates the slopes of these lines in degrees; finds the successive points where the curve has zero slope and sets these points (grey-levels) as −1 if they represent a minimum (valley in the curve) or 1 if they represent a maximum (peak in the curve); then finds the locations of peaks or valleys in the curve by finding the position of a 1 or a −1 in the array of grey-level values.

The program then sets as a cut-off value the grey-level value of pixels lying in the valley of the Luminance distribution which occurs before the last peak of the distribution (Step 413).

Using this cut-off value, the program then produces (Step 415) a second binary quantized image. This is a black-and-white image in which pixels corresponding to pixels in the Luminance image having grey-level values lower than the cut off point are set to 255 (white) and pixels corresponding to pixels in the Luminance image having grey-level values higher than the cut off point are set to 0 (black). The white blobs of this image are treated as cells while the black areas are treated as non-cellular area.

A closing filter is applied (Step 417) to the second binary quantized image; in this way holes, i.e., black dots within white regions, are closed.

The program now measures the area of the cells. If the area of any of the cells is less than 200 pixels then these cells are excluded, i.e. the pixels consisting these cells are set to pixel value 255 (black) (Step 419).

A hole fill function, found in the MIL, is applied to the remaining blobs (Step 412).

The resulting binary quantized image, after processing, is a mask whose white regions denote only cells.

Red blood cells are now distinguished from white blood cells based on the Saturation component of the HLS image. The mask is used to limit processing to only the cell areas.

The program now counts the number of pixels whose Saturation value is each possible value of Saturation. The counts are stored as an array of length 256 containing the count of pixels having a grey-level value corresponding to each index into the array (Step 423).

The program now analyzes (Step 425) the Saturation distribution curve, as represented by the values stored in the array, and locates the first peak. This peak includes pixel values that represent areas contained in white blood cells.

The grey-level value that coincides with the first minimum (valley) after the peak is set as a cut-off point (Step 427).

Using this cut-off value the program produces (Step 429) a third binary quantized image. Pixels corresponding to pixels in the Saturation image having grey-level values higher than the cut-off point are set to 255 (white). They constitute red blood cell areas. Pixels corresponding to pixels in the Saturation image having grey-level values lower than the cutoff point are set to 0 (black). The white blobs of this third binary quantized image are seeds for areas that belong to red blood cells.

A closing filter is applied (Step 431) to the third binary quantized image; in this way holes, i.e., black dots within white regions, are closed.

A hole fill function, found in the MIL, is applied (Step 433) to the remaining blobs.

The resulting binary quantized image, after processing, is a new mask that contains only white blood cells.

An erase border blob function of MIL is now applied (Step 435) to the remaining blobs, removing those which include pixels coincident with a border of the image area. Such blobs cannot be included in further processing as it is not known how much of the cell is missing when it is coincident with a border to the image area.

An erosion filter is applied 6 times to this mask; thus any connected blobs (white blood cell seeds) are disconnected (Step 437).

A "thick" filter is applied 14 times (Step 439). The "thick" filter is equivalent to a dilation filter. That is, it increases the size of a blob by successively adding a row of pixels at the periphery of the blob. If a growing blob meets an adjacent blob growing next to it, the thick filter does not connect the two growing blobs. Thus adjacent blobs can be separated.

The first binary quantized mask (containing all the cells) and the third binary quantized mask (containing the separated seeds of white blood cells) are combined with a RECONSTRUCTFROMSEED MIL operator. A fourth mask thus constructed contains blobs (cells) copied from the first mask that are allowed by the third mask and therefore represent white blood cells (Step 441).

The blobs in the fourth mask are measured for their area and compactness: Area (A) is the number of pixels in a blob; Compactness is derived from the perimeter (p) and area (A) of a blob, it is equal to: $p^2/4$ (A). The more convoluted the shape, the bigger the value. A circle has the minimum compactness value (1.0). Perimeter is the total length of edges in a blob, with an allowance made for the staircase effect which is produced when diagonal edges are digitized (inside corners are counted as 1.414, rather than 2.0). Blobs are retained in the fourth mask only if their area is between 1000 and 8000 pixels and they have a compactness less than 3, thus allowing for cells with relatively rough outline. Blobs that touch the border of the image are excluded from further processing (Step 443).

The fourth mask is applied to the Hue component in the following manner (Steps 445, 447, 449 and 451):

Pixels from the Hue component are copied to a new image retaining their Hue value, provided that their coordinates coincide with white (255) pixels in the "mask"; all other pixels in the new image are set to 0 (black) (Step 445).

The pixel values in each of the contiguous non-0 pixel areas, i.e., those blobs corresponding to images of red cells, are checked for values between 190 and 255. The number of such pixels in each blob is counted (Step 447).

If there are more than 200 such pixels, the blob represents a nucleated red blood cell. The coordinates of the center of gravity of each such cell are stored. The mask is binary quantized so that all pixels having non-0 values are set to 255 (white); and the mask is stored as a separate Tagged Image File Format (TIFF) file (Step 449).

The program moves to the next stored coordinates for a possible fetal cell which do not coincide with any of the coordinates stored during the previous step. The entire process is repeated until a preset number of nucleated red blood cells have been identified. The results, including the nucleated red blood cell coordinates and the names of the respective mask files, along with various characteristic codes for the blood slide are stored in a result text file. The nucleated red blood cells whose coordinates are stored are the fetal cells sought (Step 451).

After fetal cells are identified, the second signal is generated, for example by in situ PCR or PCR in situ hybridization or FISH, as described above.

6.2.4. Detection of the Second Signal

A smear including in situ PCR or PCR in situ hybridization treated cells is positioned on the stage (FIG. 2,201). If necessary calibration steps are taken, as before. Calibration permits the software to compensate for day to day variation in performance as well as variations from one microscope, camera, etc. to another. Detection of the second signal then proceeds, as shown in the flow chart of FIG. 5, as follows:

Magnification objective 60× (63×) is chosen (Step 501).

The x-y stage is moved to the first fetal cell position according to data from the result file compiled from detection of the first signal, as described above (Step 503).

The optical field is acquired using the CCD camera (FIG. 2,209) and transferred to the computer (FIG. 2,211) as an RGB image (Step 505).

The RGB image is transformed to the HLS model (Step 507).

The TIFF file containing the black and white mask is loaded as a separate image (Step 509).

The pixels of the Hue component not corresponding to white areas in the mask are set to 0 (black) (Step 511).

The remaining areas, which represent fetal cells, are searched for pixel values corresponding to a signal produced following PCR. For example, the signal may be a color which arises due to the presence of alkaline phosphatase, i.e., red. The non black areas of the Hue component are searched for pixel values ranging from 0 to 30 (Step 513).

The stage is moved to the next non-processed fetal cell and the above process is repeated (Step 515).

An alternative process for detecting a second signal generated using FISH is now described in greater detail.

The PC 211 executes a software program called SIMPLE which controls operation of the frame grabber and image processor circuit 217. SIMPLE also processes images captured by frame grabber and image processor circuit 217 and subsequently stores images and processed data in PC 211 as disk files. SIMPLE provides an icon-based environment with specialized routines particularly suitable for performing such image processing tasks as filtering, object selection and measurement. Most of the SIMPLE tasks are directed by a human operator using a pointing device connected to PC 211, such as a mouse or trackball (not shown).

In order to process images using SIMPLE, a number of image calibration steps must first be taken.

The flowchart of FIG. 10 shows the calibration steps of this embodiment of the present invention. Calibration modifies parameters of the software program to compensate for day to day variation in system performance, as well as variations from one microscope 205, camera 209, and other system components to another.

In particular, calibration is directed to determining image magnification so that accurate size measurements may be made. Object size measurements in SIMPLE are initially made in pixels. The operator can calibrate the image using a distance calibration standard such as a microscope graticule or other solid support, e.g., a culture plate or a well having known, fixed distances marked thereon, as follows. In step 1001, the SIMPLE Image Capture utility is loaded into the PC 211 for execution. An image of a microscope graticule slide (or other distance calibration standard) is then grabbed, step 1003, using the microscope 205 and the camera 209 using a specific, nominal total magnification, e.g., a 10× ocular and a 60× (63×) objective lens. This image is processed in the processing board. Selecting the SIMPLE CALIBRATE function, step 1005, causes a cursor to appear on the image monitor. The cursor is moved in response to operator input made using the pointing device to the start of the known distance and that point designated by the operator. The cursor is then moved, causing the SIMPLE software program to draw a rubber-band like line which the operator then joins to the other end of the known distance, whereupon that point is also designated. Then the operator answers the question "How long is the line" by entering the number of calibration units indicated by the line. A calibration factor is thus updated, step 1007. The MEASURE function may now be selected to check the calibration, step 1009. Selecting the function will cause the cursor to again appear on the monitor. The cursor is moved to the first point of a distance to be measured, which is designated, then the rubber-band line is dragged to the other end of the distance to be measured, which is designated. The measured distance is verified, step 1011. If the measured distance does not match the actual distance, then control may be returned to step 1005 to re-calibrate. Otherwise, the current calibration is saved by selecting a DISK SAVE function, step 1013. Multiple calibration files can be saved to be used in future applications, for example employing different lens combinations.

The automated analysis employs two principal procedures: a preprocessing procedure and a main procedure. Except where noted, the steps of the procedures are performed by the computer executing SIMPLE software instructions to carry out the functions named. The functions named are available directly in simple, as named commands.

A new slide properly stained using the fluorescence in situ hybridization (FISH) technique is placed under the fluorescence microscope. The objects of interest which are to be recognized, i.e., the nuclear or chromosomal areas, have specific chromatic features. Multiple targets can be delineated simultaneously in a particular specimen by combining fluorescence detection procedures. That is, if different targets are labeled with different fluorophors that fluoresce at different wavelengths, then the software program can be made to separately identify objects emitting the different fluorophors, provided full color information is available in the image. Targets with differing affinities for different fluorophors may be differentiated by the color combinations emitted. Each target may emit at wavelengths corresponding to two or more fluorophors, but the intensity of each may differ, for example. Thus, all three color components of the microscopic images are used during processing.

For each new specimen inserted under the microscope, a preprocessing procedure is first executed. The flowchart of FIG. 11 shows the preprocessing steps of this embodiment of the present invention. Preprocessing permits the software to compensate for specimen-to specimen variations.

Preprocessing produces a number of results which are required by subsequent steps performed as part of the main processing steps. These results are passed from the preprocessing steps to the main processing steps by any conventional means, such as storing them in RAM or on disk.

A microscope image is first grabbed by the frame grabber and image processing circuits (FIG. 2,217), step 1101. The specimen has been prepared and placed in the optical path of the microscope in such a way that the image grabbed includes one or more interphase nuclei or a mixture of interphase nuclei and metaphase chromosomes. Next, a region of interest (ROI) is manually selected using the pointing device, step 1103, to include intracellular, cytoplasmic and nuclear image portions, but to exclude fluorescent areas of the nucleus, i.e. interesting objects. For the regions not of interest which have been selected, maximum and minimum values of the red, green and blue components of the pixels of those regions are determined. The maximum and minimum red, green and blue values 1105 are then passed to the main processing steps. In step 1107, high and low area limits are set which define the largest and smallest chromosomal areas to be recognized. The high and low area limits are placed on a qualifier list 1109, which is also passed to the main processing steps. Also placed on the qualifier list 1109 is an indication or flag that the remove edge objects function has been set, step 1111. In subsequent processing, the remove edge objects function will cause objects whose boundaries intersect the edge of the image to be removed from the regions to be considered. The parameters of selected objects which are to be measured are then selected, step 1113, and placed on parameter list 1115. Parameter list 115 is also passed to the main processing steps. Finally, the operator selects a name for an ASCII result file in which parameter measurements are saved, step 1117. The file name, 1119, is passed to the main processing steps.

Parameters which may be selected to be measured and placed on parameter list 1115 may include such values of interest as the area of the object and the mean red, green and blue intensity values within the object. By choice of parameters to be placed on parameter list 115 and the values of qualifiers placed on qualifier list 1109. The present invention may be applied to the taking of other measurements or the making of other determinations than those to which the specific embodiment described has been applied. For example, by changing the high and low area limits placed on qualifier list 1109, objects of different sizes than the size of a chromosome may be detected. Likewise, the parameters noted in connection with the present embodiment are suitable for distinguishing between particular fluorescent labels applied to particular chromosomes and which fluoresce at different wavelengths. However, other parameters could be measured which are suitable for making other determinations concerning the detected image.

After preprocessing, the system performs the automated analysis by the repeated execution of the main procedure.

The slide containing the FISH-treated cells is positioned into the X-Y stage 201. The X-Y stage 201 is moved to an initial observation position found to contain a rare cell. A processing loop is executed repeatedly until either a predetermined number of the rare cells of a particular type have been measured. In the application for which the present embodiment is intended, identifying multiple targets of chromosomal DNA, the loop would preferably be executed until 20-100 nuclei have been processed. Each nucleus is manually selected in the successive optical fields. Data representing the measurement of the chromosomal areas within those nuclei are collected in an ASCII file.

Execution of the processing loop is controlled by the operator who selects the nuclear areas to be processed through manual delineation of a wider area containing the nucleus, i.e., a wide Region Of Interest (ROI) containing only the nuclear area in which the chromosomal areas are to be counted.

The computer instructions defining the main processing procedure are contained in a "work" file which is executed automatically. The instructions include instructions to suspend execution for the operator to select the Region of Interest containing the nucleus. The main processing procedure is now described in detail.

Using the apparatus described above in connection with the SIMPLE software system, the main processing steps first grab an image of the prepared slide, step 1201, which includes at least one nucleus containing fluorescing regions. An ROI containing a single nucleus having fluorescence regions is then selected, step 1203. The selection is conventionally performed using the pointing device. In step 1205, the image is automatically processed to select the background, or non-interesting portions of the ROI, by using the maximum and minimum red, green and blue values 1105 passed from the preprocessing procedure, step 1205. That is, those pixels whose red, green and blue intensity values fall between the maximum and minimum values obtained in preprocessing are selected as part of the background. At this point, the background is selected and the objects of interest are not selected. Therefore, a logical NOT operator is applied to the selection, causing the objects to be selected rather than the background, step 1207. A set of complex filtering steps, steps 12000, described below, are applied to generate a final selection of those areas considered interesting, in that they contain the fluorescent objects desired to be measured. The qualifier list 1109 is then applied against the characteristics of the objects remaining, to eliminate objects outside the high and low area limits and also to eliminate those objects on the edges of the region of interest, step 1209. The parameters contained on parameter list 1115 are then measured at step 1211, and the results stored, step 1213, in a result file 1215 having the file name 1119 determined by the preprocessing steps. At this point, either the operator or a counter in the software program determines whether the main processing steps have been performed a sufficient number of times, and main processing is done, step 1217. If it is determined that additional passes through the main processing steps are required, then control passes to step 1201, wherein a new image is grabbed.

The above-described main processing steps are repeated until a statistically significant number of samples have been measured. For example, in order to detect the genetic abnormality of a trisome of chromosome 21, 20-100 cell nuclei should be measured, requiring 20-100 passes through the main processing steps.

The filtering steps 12000 operate on a pixel-by-pixel basis, as follows. In step 12001, a hole filling filter is applied to the image. This filter, available through the SIMPLE language, determines when dark holes have appeared within the lighter fluorescent chromosomes by searching for dark areas within light objects. Those areas are lightened up. The output of the hole filling filter is held in a temporary image file 12101, as well as being used as the input to the erosion filter, step 12003. Erosion filtering, also available through the SIMPLE language, replaces the center pixel of a small kernel with the darkest pixel in the kernel. In the preferred embodiment, the kernel used is 3×3. A separate operation, step 12005 is next performed, to grow the objects until they meet, but do not merge. This step also creates outlines, defining the edges of all the objects. A logical NOT operation, step 12007, causes the pixels within the outlines to become selected rather than the outlines. Finally, in step 12009, the result of step 12007 is logically ANDed with the stored temporary image file 12101. This causes only those pixels which are defined in both the temporary image file 12101 and the output of step 12007 to be retained.

If a combination of fluorescence detection procedures is used, more than two chromosomal areas may be detected per nucleus. Therefore, it is possible to recognize two chromosomal areas relative to chromosomes 21, another two relative to chromosome 18, one relative to chromosome X and one relative to chromosome Y, enabling the discovery of possible numerical aberrations detected by the enumeration of hybridization signals. The enumeration of the hybridization signals is executed after completing the measurement of 20100 nuclei through an application program external to SIMPLE, compiled using CLIPPER (COMPUTER ASSOCIATES, CA). This program reads the measurement results ASCII file and classifies the chromosomal areas detected according to their RGB color combination. When two or more different fluorophors are used in combination, different combinations of RGB color values may be used to distinguish different targets, some targets of which may be labeled by more than one fluorophor. For example, targets may be stained with red and green fluorophors, but one target may receive fluorophors to emit 30% red and 70% green, another target may receive fluorophors to emit 70% red and 30% green, while a third target may receive fluorophors to emit only red. The three targets may be distinguished on the basis of their relative emissions. If the number of signals indicative of a chromosomal area corresponding to a specific chromosome, e.g., chromosome 21, is greater than two to an operator-selected statistically significant level, then a report is issued identifying an increased likelihood for trisomy 21 in the specific sample.

Although the present invention has been described in connection with the clinical detection of chromosomal abnormalities in a cell-containing sample, the image processing methods disclosed herein has other clinical applications. For example, the image processing steps described can be used to automate a urinalysis process. When the techniques of the present application are combined with those of application Ser. No. 08/132,804, filed Oct. 7, 1993, a wide variety of cell types can be visualized and analyzed, based on their morphology. Cell morphology can be observed for the purpose of diagnosing conditions for which cell morphology has been correlated to a physiological condition. Such conditions are known to those of skill in the art. See, e.g., Harrison, supra. Various cell characteristics and abnormalities may be detected based on these techniques. Finally, it should be noted that the particular source of the sample is not a limitation of the present invention, as the sample may be derived from a blood sample, a serum sample, a urine sample or a cell sample from the uterine cervix. The cell visualization and image analysis techniques described herein may be used for any condition detectable by analysis of individual cells, either by morphology or other characteristics of the isolated cells.

6.2.5. Fluorescent Microscopy

In an alternative embodiment, the first step of the process is performed using fluorescence microscopy, which enables identification of the possible rare cell positions at even lower magnification and higher processing speed compared with the method described above. The rare cells of interest are stained with a fluorescent label or fluorophore. In this embodiment, in essence, in the first stage, one is looking for dots of light. Thus, in the case of analyzing fetal cells the light dots can be produced by an antibody binding to a specific fetal hemoglobin. For example, antibodies specific for human fetal hemoglobin (Research Diagnostics Inc., NJ) and for embryonic epsilon hemoglobin chain (Immuno-Rx, GA) are commercially available and can be used as fluorescently labeled antibodies or a fluorescent signal can be generated by use of a fluorescently labeled secondary antibody. Fluorescent light can be produced by other types of stains or labels for rare cells, as known in the art. Fluorescent staining of the type required for this processing step is known in the art, and will not be discussed in further detail. Because of this simplification, one can use magnification, such as 1 Ox or possibly lower, and need not even employ color cameras at this stage, since the algorithm will only be looking for blobs having high light intensity.

It will be appreciated that the first processing step in accordance with this embodiment of the invention can be performed very efficiently and at a high processing speed. Further, modifications to the generic processing algorithm illustrated in FIG. 3 will be apparent, and need not be discussed. High-resolution imaging of the candidate cells identified in the first step, and staining for biologically important second signal can be applied as described in the proceeding sections.

6.3. Variations

A number of variations on the above-described system and method are also contemplated and are encompassed by the present invention. Some of these are now described. This description will also suggest others to those skilled in the art.

Each unenriched blood sample may be used to prepare smears on each of a plurality of individual microscope slides. When prepared in this way, each slide can undergo detection of the first signal. However, only those slides which the first signal is detected need be further processed to generate the second signal, and subsequently are analyzed to detect the second signal. Processing in this way permits the use of conventional sample and slide-handling equipment.

In a variation illustrated schematically in FIG. 6, the unenriched blood sample 601 is used to prepare a single, long smear on a flexible substrate 603. The substrate 603 can have a length 10 or more times its width. For example, a strip of cellulose acetate film base with sprocket holes on either side could be used as the substrate. The strip carrying the smear undergoes the processing steps described above in a continuous processing system, as shown in FIG. 6. After locations of fetal cells are determined by detection of the first signal, segments of the smear including those locations are cut out of the continuous strip for generation and detection of the second signal.

In an alternative processing method using a single, long smear on a flexible substrate, the strip is divided into a plurality of individual segments similar to microscope slides, before generating and detecting the first signal. Processing proceeds as for individual microscope slides.

The above variations, and similar variations, are advantageous in that the entire smear need not be processed for generation and detection of the second signal. Only those slides or segments in which the first signal is detected need undergo the further processing to generate and detect the second signal.

In one aspect of the invention, a device is provided for dispensing reagents only to those portions of the smear where a rare cell is detected. Referring to FIG. 7, an apparatus of the invention is shown including a reagent dispenser system. The reagent dispenser system can be located for dispensing reagents to precise locations on the stage. This is particularly suited for dispensing reagents only of the coordinates identified by a first signal, such as the coordinates of a rare cell (e.g., a fetal cell and a maternal blood smear). The system includes a reagent dispenser 701 which is a housing for one or more micropipettes located within the housing. The reagent dispenser is attached in this embodiment to the microscope and is positioned relative to the stage in fixed relation to the microscope. The narrow tip of the reagent dispenser 701 is adjacent the stage 201. The opposite end of the reagent dispenser 701 has communicating therewith feedline 703 which is a tube or a housing carrying a plurality of tubes for delivering reagents to the reagent dispenser 701. The feedline 703 is attached remote from the reagent dispenser 701 to a first reagent container 705 and a second reagent container 707. In the embodiment shown, the feedline 703 is a housing through which passes feedline 703' communicating with reagent container 705 and feedline 703' communicating with reagent container 707. A pump 709 is attached to feedline 703" for pumping reagent from the reagent container 707 to the reagent dispenser 701, and out the narrow tip of the reagent dispenser 701 onto the stage at a desired location. Another pump 709' is attached to feedline 703' for delivering reagents from reagent container 705 to the reagent dispenser 701. The pumps are electronically controlled by PC 211 using specifically compiled software commands indicated by "reagent control". The reagents can be any one of the reagents described above in connection with generating a signal.

In the embodiment shown, the reagent dispenser is attached to the microscope. The reagent dispenser need not be attached to the microscope and, instead, can be otherwise attached to any frame relative to the X-Y stage. The stage is shown as moving with respect to the reagent dispenser for locating the narrow tip of the reagent dispenser at a precise location with respect to a slide on the stage. The slide on the stage can be moved to a different location, and the reagent dispenser can be itself moveably controlled to locate it relative to a set of coordinates in the slide. What is important is that, in an automated fashion, the coordinates of a detected rare cell can be positioned with respect to the dispensing end of the reagent dispenser, whereby materials may be delivered to a discrete location at the coordinates of the rare cell. If the reagent dispenser is controlled by a motor and moveable with respect to a stage or a slide upon a stage, then the reagent dispenser can be provided with a sensor for locating its position with respect to the slide or stage. Thus, the slide on a stage can be processed in series, with the microscope first locating the coordinates on the slide of the rare cell. The slide then is next moved to a second processing area where the reagent dispenser is positioned at the previously-identified coordinates in the slide and reagents are delivered to generate the second signal. Optionally the slide could be moved to a third station, such as a thermocycling station and then back to the microscope field for viewing.

It should be evident that different treatments of the smear are possible when it is desired to identify a different cell type or to diagnose a different cellular characteristic. The biochemistry, morphological parameters and colors described above may each be varied in known ways to meet other diagnostic needs.

Computer and image processing technologies are constantly changing. Newer technologies which meet the needs of the above-described methods and apparatus, while not specifically described here, are clearly contemplated as within the invention. For example, certain conventional pixel and image file formats are mentioned above, but others may also be used. Image files may be compressed using JPEG or GIF techniques now known in the art or other techniques yet to be developed. Processing may be performed in an RGB color description space instead of the HLS space currently used. Other color spaces may also be used, as desired by the skilled artisan, particularly when detection of a sought-after characteristic is enhanced thereby.

While the embodiments of the invention have been described in connection with unenriched samples of maternal blood, aspects of the invention may be practiced on conventionally enriched or partially enriched maternal blood samples, as well. The use of a computer-controlled microscopic vision system to identify and to diagnose fetal cells within the sample is applicable to samples covering a full range of fetal cell concentrations. As has been discussed above, the use of such a system is particularly advantageous when used in connection with unenriched maternal blood samples.

The present invention has now been described in connection with a number of particular embodiments thereof. Additional variations should now be evident to those skilled in the art, and are contemplated as falling within the scope of the invention, which is limited only by the claims appended hereto and equivalents thereof.

What is claimed is:

1. A method in a computer system comprising the steps of:
   detecting on a microscope slide of a cell sample monolayer containing one or more rare cells;
   employing detectors, determining in an automated sequence of steps a first signal indicative of the position of rare cell(s) on said microscope slide;
   using said determined position of said rare cell(s) to automatically position a dispensing system over said determined position;
   dispensing from said dispensing system a diagnostic label having diagpositic significance to said rare cell(s) in situ;
   determining if there is the presence of a second signal indicative of said diagnostic label being bound to said rare cell(s).

2. The method of claim 1, wherein the sample of cells are derived from maternal blood and rare cell(s) is a fetal cell.

3. A method of obtaining an image signal of a rare cell found on a substrate surface, in accordance with claim 1, wherein the step of determining the position of said rare cell based upon detection of pre-determined parameters associated with said rare cell(s) is performed by a computerized automated microscopy system.

4. The method of claim 3, wherein said computerized automated microscopy system used has two or more objectives.

5. A method of obtaining an image signal of a rare cell found on a substrate surface, in accordance with claim 1, wherein the step of treating said cell sample with a diagnostic label by a label or stain dispensing system is performed by a computerized label or stain dispensing system.

6. A method of obtaining an image signal of a rare cell found on a substrate surface, in accordance with claim 1, wherein the step of detecting whether a signal indicative of said diagnostic label is associated with said determined position of said rare cell(s) is performed by a computerized automated microscopy system.

7. The method of claim 6, wherein said computerized automated microscopy system has two or more objectives.

8. A method of obtaining an image signal of a rare cell found on a substrate surface, in accordance with claim 1, wherein the step o providing a diagnosis based on detection of said diagnostic label being associated with the position of one or more detected rare cell(s), further comprises the step of recording said rare cell(s) position in a computer memory.

9. A method of obtaining an image signal of a rare cell found on a substrate surface, in accordance with claim 1, wherein said cell sample is enriched by an increased rare cell concentration.

10. A method in a computer system, in accordance with claim 1, further comprising providing a putative diagnosis if a second signal, indicative of said second diagnostic label being bound to said rare cell(s), is detected.

11. A computer implemented method of automatically obtaining from a sample of maternal blood containing an unnaturally present concentration of fetal cells, a signal having diagnostic significance relative to the fetal cells, said method comprising an automatically implemented sequence of the steps of:
   preparing a smear of the sample of maternal blood on a substrate;
   acquiring/observing the smear image using a computerized microscopic vision system operatively configured to read record said substrate and to obtain a first signal indicative of the presence of a fetal cell;
   contacting the fetal cell with an agent to generate a second signal, the second signal having said diagnostic significance;

acquiring/observing the fetal cell using the computerized microscopic vision system to record/obtain the second signal; and counting occurrences of the second signal in a plurality of fetal cells emitting said first signal.

12. The method of claim 11, wherein the first signal is further processed to represent morphological measurements of the fetal cells.

13. The method of claim 11, wherein the first signal and the second signal do not mask one another when both are present.

14. The method of claim 11, further comprising the step of: calibrating a coordinate system to said substrate so that coordinates of said fetal cell(s) identified at one point in time can be returned to at a later point of time.

15. The method of claim 11, wherein said computerized microscopic vision system has two or more objectives.

16. A computer implemented method, in accordance with claim 11, wherein said sample of maternal blood is enriched by an increased rare cell concentration.

* * * * *

UNITED STATES PATENT AND TRADEMARK OFFICE
CERTIFICATE OF CORRECTION

PATENT NO. : 7,522,757 B2  Page 1 of 1
APPLICATION NO. : 11/264273
DATED : April 21, 2009
INVENTOR(S) : Tsipouras et al.

It is certified that error appears in the above-identified patent and that said Letters Patent is hereby corrected as shown below:

COLUMN 40,
Line 33, now reads:

"wherein the step o providing a diagnosis based on detection of"

COLUMN 40,
Line 33, should read as follows:

-- wherein the step of providing a diagnosis based on detection of --

Signed and Sealed this

Sixteenth Day of June, 2009

JOHN DOLL
*Acting Director of the United States Patent and Trademark Office*